(12) United States Patent
Bronstein et al.

(10) Patent No.: US 8,500,451 B2
(45) Date of Patent: Aug. 6, 2013

(54) PREOPERATIVE SURGICAL SIMULATION

(75) Inventors: Ran Bronstein, Modiln (IL); Niv Fisher, Herzlia (IL); Ofek Shilon, Sde Hemed (IL)

(73) Assignee: Simbionix Ltd., Lod (IL)

( * ) Notice: Subject to any disclaimer, the term of this patent is extended or adjusted under 35 U.S.C. 154(b) by 498 days.

(21) Appl. No.: 12/224,314

(22) PCT Filed: Jan. 13, 2008

(86) PCT No.: PCT/IL2008/000056
§ 371 (c)(1),
(2), (4) Date: Aug. 22, 2008

(87) PCT Pub. No.: WO2008/087629
PCT Pub. Date: Jul. 24, 2008

(65) Prior Publication Data
US 2009/0018808 A1    Jan. 15, 2009

Related U.S. Application Data

(60) Provisional application No. 60/880,415, filed on Jan. 16, 2007.

(51) Int. Cl.
*G09B 23/28* (2006.01)

(52) U.S. Cl.
USPC ............................ 434/262; 434/267; 434/272

(58) Field of Classification Search
USPC .................. 434/262, 267, 272; 600/109, 416, 600/449
See application file for complete search history.

(56) References Cited

U.S. PATENT DOCUMENTS

| | | | |
|---|---|---|---|
| 1,959,490 A | 5/1934 | Mistelski |
| 3,024,539 A | 3/1962 | Rider |
| 3,263,824 A | 8/1966 | Jones et al. |
| 3,406,601 A | 10/1968 | Clifford |
| 3,490,059 A | 1/1970 | Paulsen et al. |
| 3,517,446 A | 6/1970 | Corlyon et al. |
| 3,520,071 A | 7/1970 | Abrahamson et al. |
| 3,573,444 A | 4/1971 | Kawabata et al. |
| 3,579,842 A | 5/1971 | Scher |
| 3,704,529 A | 12/1972 | Cioppa |

(Continued)

FOREIGN PATENT DOCUMENTS

| | | |
|---|---|---|
| EP | 0 147 516 | 3/1988 |
| EP | 0 265 011 | 4/1988 |

(Continued)

OTHER PUBLICATIONS

International Search Report for International Publication No. PCT/IL2009/000056 date of mailing Feb. 4, 2009.

(Continued)

*Primary Examiner* — Xuan Thai
*Assistant Examiner* — Bruk Gebremichael
(74) *Attorney, Agent, or Firm* — Pearl Cohen Zedek Latzer, LLP

(57) ABSTRACT

An apparatus for simulating an image-guided procedure. The system comprises an input for receiving a three-dimensional (3D) medical image depicting an organ of a patient, a model generation unit for generating a 3D anatomical model of the organ according to the 3D medical image, and a simulating unit for simulating a planned image-guided procedure on the patient, according to the 3D anatomical model.

22 Claims, 6 Drawing Sheets

U.S. PATENT DOCUMENTS

| | | | |
|---|---|---|---|
| 3,722,108 A | 3/1973 | Chase | |
| 3,739,276 A | 6/1973 | Dornberger | |
| 3,775,865 A | 12/1973 | Rowan | |
| 3,789,518 A | 2/1974 | Chase | |
| 3,795,061 A | 3/1974 | Sarnoff et al. | |
| 3,795,150 A | 3/1974 | Eckhardt | |
| 3,814,145 A | 6/1974 | Gott et al. | |
| 3,861,065 A | 1/1975 | Courtenay et al. | |
| 3,875,488 A | 4/1975 | Crocker et al. | |
| 3,919,691 A | 11/1975 | Noll | |
| 3,945,593 A | 3/1976 | Schanzer | |
| 3,991,490 A | 11/1976 | Markman | |
| 4,024,473 A | 5/1977 | Edge et al. | |
| 4,024,873 A | 5/1977 | Antoshkiw et al. | |
| 4,033,331 A | 7/1977 | Guss et al. | |
| 4,078,317 A | 3/1978 | Wheatley et al. | |
| 4,089,494 A | 5/1978 | Anderson et al. | |
| 4,115,755 A | 9/1978 | Cotton | |
| 4,136,554 A | 1/1979 | Larson | |
| 4,148,014 A | 4/1979 | Burson | |
| 4,162,582 A | 7/1979 | McGraw et al. | |
| 4,177,984 A | 12/1979 | Douglas et al. | |
| 4,182,054 A | 1/1980 | Wise et al. | |
| 4,183,249 A | 1/1980 | Anderson | |
| 4,227,319 A | 10/1980 | Guy et al. | |
| 4,236,685 A | 12/1980 | Kissel | |
| 4,250,636 A | 2/1981 | Horwitz | |
| 4,250,887 A | 2/1981 | Dardik et al. | |
| 4,262,549 A | 4/1981 | Schwellenbach | |
| 4,264,312 A | 4/1981 | Cianci | |
| 4,276,702 A | 7/1981 | Horwitz | |
| 4,307,539 A | 12/1981 | Klein | |
| 4,333,070 A | 6/1982 | Barnes | |
| 4,334,216 A | 6/1982 | Lacroix | |
| 4,360,345 A | 11/1982 | Hon | |
| 4,398,889 A | 8/1983 | Lam et al. | |
| 4,427,388 A | 1/1984 | Hope | |
| 4,436,188 A | 3/1984 | Jones | |
| 4,459,113 A | 7/1984 | Boscaro Gatti et al. | |
| 4,464,117 A | 8/1984 | Foerst | |
| 4,478,407 A | 10/1984 | Manabe | |
| 4,481,001 A | 11/1984 | Graham et al. | |
| 4,504,233 A | 3/1985 | Galus et al. | |
| 4,513,235 A | 4/1985 | Acklam et al. | |
| 4,545,390 A | 10/1985 | Leary | |
| 4,550,617 A | 11/1985 | Fraignier et al. | |
| 4,551,101 A | 11/1985 | Neumann | |
| 4,573,452 A | 3/1986 | Greenberg | |
| 4,599,070 A | 7/1986 | Hladky et al. | |
| 4,604,016 A | 8/1986 | Joyce | |
| 4,605,373 A | 8/1986 | Rosen | |
| 4,632,341 A | 12/1986 | Repperger et al. | |
| 4,642,055 A | 2/1987 | Saliterman | |
| 4,646,742 A | 3/1987 | Packard et al. | |
| 4,654,648 A | 3/1987 | Herrington et al. | |
| 4,655,673 A | 4/1987 | Hawkes | |
| 4,659,313 A | 4/1987 | Kuster et al. | |
| 4,667,182 A | 5/1987 | Murphy | |
| 4,688,983 A | 8/1987 | Lindbom | |
| 4,706,006 A | 11/1987 | Solomon | |
| 4,708,650 A | 11/1987 | Holewinski et al. | |
| 4,708,656 A | 11/1987 | de Vries et al. | |
| 4,712,101 A | 12/1987 | Culver | |
| 4,713,007 A | 12/1987 | Alban | |
| 4,726,772 A | 2/1988 | Amplatz | |
| 4,733,214 A | 3/1988 | Andresen | |
| 4,742,815 A | 5/1988 | Ninan et al. | |
| 4,748,984 A | 6/1988 | Patel | |
| 4,751,662 A | 6/1988 | Crosbie | |
| 4,757,302 A | 7/1988 | Hatakeyama et al. | |
| 4,769,763 A | 9/1988 | Trieb et al. | |
| 4,775,289 A | 10/1988 | Kazerooni | |
| 4,782,327 A | 11/1988 | Kley et al. | |
| 4,786,892 A | 11/1988 | Kubo et al. | |
| 4,789,340 A | 12/1988 | Zikria | |
| 4,794,384 A | 12/1988 | Jackson | |
| 4,795,296 A | 1/1989 | Jau | |
| 4,797,104 A | 1/1989 | Laerdal et al. | |
| 4,803,413 A | 2/1989 | Kendig et al. | |
| 4,820,162 A | 4/1989 | Ross | |
| 4,823,634 A | 4/1989 | Culver | |
| 4,825,875 A | 5/1989 | Ninan et al. | |
| 4,839,838 A | 6/1989 | LaBiche et al. | |
| 4,857,881 A | 8/1989 | Hayes | |
| 4,860,215 A | 8/1989 | Seraji | |
| 4,865,423 A | 9/1989 | Doi | |
| 4,867,685 A | 9/1989 | Brush et al. | |
| 4,868,549 A | 9/1989 | Affinito et al. | |
| 4,870,964 A | 10/1989 | Bailey, Jr. et al. | |
| 4,874,998 A | 10/1989 | Hollis, Jr. | |
| H703 H | 11/1989 | Repperger et al. | |
| 4,879,556 A | 11/1989 | Duimel | |
| 4,881,324 A | 11/1989 | Khinchuk | |
| 4,885,565 A | 12/1989 | Embach | |
| 4,887,966 A | 12/1989 | Gellerman | |
| 4,891,764 A | 1/1990 | McIntosh | |
| 4,896,554 A | 1/1990 | Culver | |
| 4,907,796 A | 3/1990 | Roel-Rodriguez | |
| 4,907,970 A | 3/1990 | Meenen | |
| 4,907,973 A | 3/1990 | Hon | |
| 4,909,232 A | 3/1990 | Carella | |
| 4,912,638 A | 3/1990 | Pratt | |
| 4,930,770 A | 6/1990 | Baker | |
| 4,934,694 A | 6/1990 | McIntosh | |
| 4,940,234 A | 7/1990 | Ishida et al. | |
| 4,949,119 A | 8/1990 | Moncrief et al. | |
| 4,955,654 A | 9/1990 | Tsuchihashi et al. | |
| 4,961,138 A | 10/1990 | Gorniak | |
| 4,961,267 A | 10/1990 | Herzog | |
| 4,964,097 A | 10/1990 | Wang et al. | |
| 4,975,546 A | 12/1990 | Craig | |
| 4,982,618 A | 1/1991 | Culver | |
| 4,982,918 A | 1/1991 | Kaye | |
| 4,998,916 A | 3/1991 | Hammerslag et al. | |
| 5,004,391 A | 4/1991 | Burdea | |
| 5,007,300 A | 4/1991 | Siva | |
| 5,009,598 A | 4/1991 | Bennington | |
| 5,018,922 A | 5/1991 | Yoshinada et al. | |
| 5,019,761 A | 5/1991 | Kraft | |
| 5,021,982 A | 6/1991 | Crosbie et al. | |
| 5,022,384 A | 6/1991 | Freels et al. | |
| 5,033,352 A | 7/1991 | Kellogg et al. | |
| 5,044,956 A | 9/1991 | Behensky et al. | |
| 5,048,508 A | 9/1991 | Storz | |
| 5,057,078 A | 10/1991 | Foote et al. | |
| 5,062,594 A | 11/1991 | Repperger | |
| 5,072,361 A | 12/1991 | Davis et al. | |
| 5,077,769 A | 12/1991 | Franciose | |
| 5,078,152 A | 1/1992 | Bond et al. | |
| 5,086,296 A | 2/1992 | Clark | |
| 5,103,404 A | 4/1992 | McIntosh | |
| 5,104,328 A | 4/1992 | Lounsbury | |
| 5,112,228 A | 5/1992 | Zouras | |
| 5,116,051 A | 5/1992 | Moncrief et al. | |
| 5,116,180 A | 5/1992 | Fung et al. | |
| 5,125,843 A | 6/1992 | Holloway | |
| 5,126,948 A | 6/1992 | Mitchell et al. | |
| 5,135,488 A | 8/1992 | Foote et al. | |
| 5,139,261 A | 8/1992 | Openiano | |
| 5,142,931 A | 9/1992 | Menahem | |
| 5,143,505 A | 9/1992 | Burdea et al. | |
| 5,146,566 A | 9/1992 | Hollis, Jr. et al. | |
| 5,149,270 A | 9/1992 | McKeown | |
| 5,153,716 A | 10/1992 | Smith | |
| 5,158,459 A | 10/1992 | Edelberg | |
| 5,167,159 A | 12/1992 | Lucking | |
| 5,171,299 A | 12/1992 | Heitzmann et al. | |
| 5,177,473 A | 1/1993 | Drysdale | |
| 5,180,351 A | 1/1993 | Ehrenfried | |
| 5,181,181 A | 1/1993 | Glynn | |
| 5,184,306 A | 2/1993 | Erdman et al. | |
| 5,184,319 A | 2/1993 | Kramer | |
| 5,185,561 A | 2/1993 | Good et al. | |
| 5,186,629 A | 2/1993 | Rohen | |
| 5,189,355 A | 2/1993 | Larkins et al. | |
| 5,191,320 A | 3/1993 | MacKay | |
| 5,193,963 A | 3/1993 | McAffee et al. | |

| | | | | | |
|---|---|---|---|---|---|
| 5,196,017 A | 3/1993 | Silva et al. | 5,451,924 A | 9/1995 | Massimino et al. |
| 5,197,003 A | 3/1993 | Moncrief et al. | 5,459,382 A | 10/1995 | Jacobus et al. |
| 5,203,563 A | 4/1993 | Loper, III | 5,461,711 A | 10/1995 | Wang et al. |
| 5,204,600 A | 4/1993 | Kahkoska | 5,467,441 A | 11/1995 | Stone et al. |
| 5,209,131 A | 5/1993 | Baxter | 5,467,763 A | 11/1995 | McMahon et al. |
| 5,209,661 A | 5/1993 | Hildreth et al. | 5,470,232 A | 11/1995 | Kelso et al. |
| 5,212,473 A | 5/1993 | Louis | 5,473,235 A | 12/1995 | Lance et al. |
| 5,215,523 A | 6/1993 | Williams et al. | 5,482,051 A | 1/1996 | Reddy et al. |
| 5,220,260 A | 6/1993 | Schuler | 5,492,530 A | 2/1996 | Fischell et al. |
| 5,222,893 A | 6/1993 | Hardesty | 5,506,605 A | 4/1996 | Paley |
| 5,223,776 A | 6/1993 | Radke et al. | 5,512,919 A | 4/1996 | Araki |
| 5,228,356 A | 7/1993 | Chuang | 5,515,078 A | 5/1996 | Greschler et al. |
| 5,240,417 A | 8/1993 | Smithson et al. | 5,524,637 A | 6/1996 | Erickson |
| 5,243,266 A | 9/1993 | Kasagami et al. | 5,541,831 A | 7/1996 | Thomas |
| 5,246,007 A | 9/1993 | Frisbie et al. | 5,542,672 A | 8/1996 | Meredith |
| 5,247,432 A | 9/1993 | Ueda | 5,542,676 A | 8/1996 | Howe, Jr. et al. |
| 5,252,068 A | 10/1993 | Gryder | 5,547,382 A | 8/1996 | Yamasaki et al. |
| 5,252,070 A | 10/1993 | Jarrett | 5,548,694 A | 8/1996 | Frisken |
| 5,257,462 A | 11/1993 | Buttermann | 5,553,198 A | 9/1996 | Wang et al. |
| 5,259,626 A | 11/1993 | Ho | 5,559,412 A | 9/1996 | Schuler |
| 5,259,894 A | 11/1993 | Sampson | 5,565,840 A | 10/1996 | Thorner et al. |
| 5,264,768 A | 11/1993 | Gregory et al. | 5,575,761 A | 11/1996 | Hajianpour |
| 5,265,034 A | 11/1993 | Breckenridge et al. | 5,577,981 A | 11/1996 | Jarvik |
| 5,269,519 A | 12/1993 | Malone | 5,580,249 A | 12/1996 | Jacobsen et al. |
| 5,275,174 A | 1/1994 | Cook | 5,584,701 A | 12/1996 | Lampotang et al. |
| 5,275,565 A | 1/1994 | Moncrief | 5,587,937 A | 12/1996 | Massie et al. |
| 5,279,309 A | 1/1994 | Taylor | 5,591,924 A | 1/1997 | Hilton |
| 5,279,563 A | 1/1994 | Brucker et al. | 5,592,401 A | 1/1997 | Kramer |
| 5,280,265 A | 1/1994 | Kramer et al. | 5,599,301 A | 2/1997 | Jacobs et al. |
| 5,283,970 A | 2/1994 | Aigner | 5,600,348 A | 2/1997 | Bartholow et al. |
| 5,286,203 A | 2/1994 | Fuller et al. | 5,607,157 A | 3/1997 | Nagashima |
| 5,295,694 A | 3/1994 | Levin | 5,607,308 A | 3/1997 | Copperman et al. |
| 5,296,846 A | 3/1994 | Ledley | 5,609,485 A | 3/1997 | Bergman et al. |
| 5,296,871 A | 3/1994 | Paley | 5,609,607 A | 3/1997 | Hechtenberg et al. |
| 5,305,203 A | 4/1994 | Raab | 5,616,030 A | 4/1997 | Watson |
| 5,309,140 A | 5/1994 | Everett, Jr. et al. | 5,623,582 A | 4/1997 | Rosenberg |
| 5,311,422 A | 5/1994 | Loftin et al. | 5,625,551 A | 4/1997 | Mitarai et al. |
| 5,313,230 A | 5/1994 | Venolia et al. | 5,625,576 A | 4/1997 | Massie et al. |
| 5,313,568 A | 5/1994 | Wallace et al. | 5,629,594 A | 5/1997 | Jacobus et al. |
| 5,314,339 A | 5/1994 | Aponte | 5,631,861 A | 5/1997 | Kramer |
| 5,317,689 A | 5/1994 | Nack et al. | 5,631,973 A | 5/1997 | Green |
| 5,318,533 A | 6/1994 | Adams et al. | 5,643,087 A | 7/1997 | Marcus et al. |
| 5,324,260 A | 6/1994 | O'Neill et al. | 5,651,775 A | 7/1997 | Walker et al. |
| 5,327,790 A | 7/1994 | Levin et al. | 5,657,429 A | 8/1997 | Wang et al. |
| 5,334,027 A | 8/1994 | Wherlock | 5,661,253 A | 8/1997 | Aoki |
| 5,335,557 A | 8/1994 | Yasutake | 5,661,667 A | 8/1997 | Rueb et al. |
| 5,344,354 A | 9/1994 | Wiley | 5,666,473 A | 9/1997 | Wallace |
| 5,353,242 A | 10/1994 | Crosbie et al. | 5,669,818 A | 9/1997 | Thorner et al. |
| 5,354,162 A | 10/1994 | Burdea et al. | 5,676,157 A | 10/1997 | Kramer |
| 5,355,148 A | 10/1994 | Anderson | 5,680,590 A | 10/1997 | Parti |
| 5,364,271 A | 11/1994 | Aknin et al. | 5,684,722 A | 11/1997 | Thorner et al. |
| 5,366,376 A | 11/1994 | Copperman et al. | 5,691,898 A | 11/1997 | Rosenberg et al. |
| 5,368,484 A | 11/1994 | Copperman et al. | 5,694,013 A | 12/1997 | Stewart et al. |
| 5,368,487 A | 11/1994 | Medina | 5,695,500 A | 12/1997 | Taylor et al. |
| 5,368,565 A | 11/1994 | DeLong | 5,701,140 A | 12/1997 | Rosenberg et al. |
| 5,370,535 A | 12/1994 | Prendergast | 5,709,219 A | 1/1998 | Chen et al. |
| 5,371,778 A | 12/1994 | Yanof et al. | 5,716,016 A | 2/1998 | Iwade et al. |
| 5,379,663 A | 1/1995 | Hara | 5,720,619 A | 2/1998 | Fisslinger |
| 5,382,885 A | 1/1995 | Salcudean et al. | 5,724,264 A | 3/1998 | Rosenberg et al. |
| 5,384,460 A | 1/1995 | Tseng | 5,731,804 A | 3/1998 | Rosenberg |
| 5,385,549 A | 1/1995 | Lampropoulos et al. | 5,736,978 A | 4/1998 | Hasser et al. |
| 5,389,865 A | 2/1995 | Jacobus et al. | 5,739,811 A | 4/1998 | Rosenberg et al. |
| 5,396,267 A | 3/1995 | Bouton | 5,742,278 A | 4/1998 | Chen et al. |
| 5,397,308 A | 3/1995 | Ellis et al. | 5,749,853 A | 5/1998 | O'Donnell et al. |
| 5,397,323 A | 3/1995 | Taylor et al. | 5,755,577 A | 5/1998 | Gillio |
| 5,399,091 A | 3/1995 | Mitsumoto | 5,766,016 A | 6/1998 | Sinclair et al. |
| 5,402,801 A | 4/1995 | Taylor | 5,769,640 A | 6/1998 | Jacobus et al. |
| 5,403,191 A | 4/1995 | Tuason | 5,771,181 A | 6/1998 | Moore et al. |
| 5,412,189 A | 5/1995 | Cragun | 5,776,050 A | 7/1998 | Chen et al. |
| 5,412,880 A | 5/1995 | Raab | 5,776,126 A | 7/1998 | Wilk et al. |
| 5,414,337 A | 5/1995 | Schuler | 5,781,172 A | 7/1998 | Engel et al. |
| 5,423,754 A | 6/1995 | Cornelius et al. | 5,797,900 A | 8/1998 | Madhani et al. |
| 5,425,644 A | 6/1995 | Szinicz | 5,800,179 A | 9/1998 | Bailey |
| 5,425,709 A | 6/1995 | Gambale | 5,805,140 A | 9/1998 | Rosenberg et al. |
| 5,428,748 A | 6/1995 | Davidson et al. | 5,806,521 A | 9/1998 | Morimoto et al. |
| 5,429,140 A | 7/1995 | Burdea et al. | 5,807,377 A | 9/1998 | Madhani et al. |
| 5,430,665 A | 7/1995 | Jin et al. | 5,808,665 A | 9/1998 | Green |
| 5,436,640 A | 7/1995 | Reeves | 5,810,007 A | 9/1998 | Holupka et al. |
| 5,445,166 A | 8/1995 | Taylor | 5,821,920 A | 10/1998 | Rosenberg et al. |

| | | | |
|---|---|---|---|
| 5,831,408 A | 11/1998 | Jacobus et al. | |
| 5,844,392 A | 12/1998 | Peurach et al. | |
| 5,882,206 A | 3/1999 | Gillio | |
| 5,889,670 A | 3/1999 | Schuler et al. | |
| 5,889,672 A | 3/1999 | Schuler et al. | |
| 5,930,741 A | 7/1999 | Kramer | |
| 5,945,978 A | 8/1999 | Holmes | |
| 5,956,484 A | 9/1999 | Rosenberg et al. | |
| 5,986,643 A | 11/1999 | Harvill et al. | |
| 5,999,185 A | 12/1999 | Kato et al. | |
| 6,004,134 A | 12/1999 | Marcus et al. | |
| 6,024,576 A | 2/2000 | Bevirt et al. | |
| 6,037,927 A | 3/2000 | Rosenberg | |
| 6,038,488 A | 3/2000 | Barnes et al. | |
| 6,042,555 A | 3/2000 | Kramer et al. | |
| 6,047,080 A * | 4/2000 | Chen et al. | 382/128 |
| 6,050,962 A | 4/2000 | Kramer et al. | |
| 6,059,506 A | 5/2000 | Kramer | |
| 6,062,865 A | 5/2000 | Bailey | |
| 6,062,866 A | 5/2000 | Prom | |
| 6,084,587 A | 7/2000 | Tarr et al. | |
| 6,088,017 A | 7/2000 | Tremblay et al. | |
| 6,104,379 A | 8/2000 | Petrich et al. | |
| 6,110,130 A | 8/2000 | Kramer | |
| 6,111,577 A | 8/2000 | Zilles et al. | |
| 6,120,465 A | 9/2000 | Guthrie et al. | |
| 6,148,280 A | 11/2000 | Kramer | |
| 6,160,489 A | 12/2000 | Perry et al. | |
| 6,162,190 A | 12/2000 | Kramer | |
| 6,195,592 B1 | 2/2001 | Schuler | |
| 6,219,032 B1 | 4/2001 | Rosenberg et al. | |
| 6,222,523 B1 | 4/2001 | Harvill et al. | |
| 6,239,784 B1 | 5/2001 | Holmes | |
| 6,275,213 B1 | 8/2001 | Tremblay et al. | |
| 6,323,837 B1 | 11/2001 | Rosenberg | |
| 6,413,229 B1 | 7/2002 | Kramer et al. | |
| 6,428,490 B1 | 8/2002 | Kramer et al. | |
| 6,497,672 B2 | 12/2002 | Kramer | |
| 6,538,634 B1 | 3/2003 | Chui et al. | |
| RE38,242 E | 9/2003 | Engel et al. | |
| 6,876,891 B1 | 4/2005 | Schuler et al. | |
| 6,885,361 B1 | 4/2005 | Harvill et al. | |
| 7,215,326 B2 | 5/2007 | Rosenberg | |
| 7,681,579 B2 | 3/2010 | Schwartz | |
| 2002/0072814 A1 | 6/2002 | Schuler et al. | |
| 2002/0107573 A1* | 8/2002 | Steinberg | 623/17.12 |
| 2002/0168618 A1* | 11/2002 | Anderson et al. | 434/262 |
| 2003/0032876 A1 | 2/2003 | Chen et al. | |
| 2003/0069719 A1 | 4/2003 | Cunningham et al. | |
| 2004/0009459 A1 | 1/2004 | Anderson et al. | |
| 2004/0015070 A1* | 1/2004 | Liang et al. | 600/407 |
| 2004/0086175 A1* | 5/2004 | Parker et al. | 382/154 |
| 2004/0234933 A1* | 11/2004 | Dawson et al. | 434/262 |
| 2005/0196740 A1* | 9/2005 | Moriyama | 434/262 |
| 2006/0173338 A1* | 8/2006 | Ma et al. | 600/456 |
| 2006/0211940 A1* | 9/2006 | Antonelli et al. | 600/410 |
| 2006/0290695 A1* | 12/2006 | Salomie | 345/420 |
| 2007/0027733 A1* | 2/2007 | Bolle et al. | 705/7 |
| 2007/0043285 A1 | 2/2007 | Schwartz | |
| 2007/0049817 A1 | 3/2007 | Preiss et al. | |
| 2007/0148625 A1 | 6/2007 | Biltz et al. | |
| 2007/0231779 A1* | 10/2007 | Santhanam et al. | 434/262 |
| 2009/0310847 A1 | 12/2009 | Matsuzaki et al. | |
| 2011/0092804 A1 | 4/2011 | Schoenefeld et al. | |

FOREIGN PATENT DOCUMENTS

| | | |
|---|---|---|
| EP | 0 393 683 | 10/1990 |
| EP | 0 456 103 | 11/1991 |
| EP | 0 489 469 | 6/1992 |
| EP | 0 316 763 | 8/1992 |
| EP | 0 567 215 | 10/1993 |
| EP | 0 571 827 | 12/1993 |
| EP | 0 624 861 | 11/1994 |
| EP | 0 626 634 | 11/1994 |
| EP | 0 623 066 | 7/1997 |
| EP | 0 632 709 | 3/2002 |
| FR | 2592514 A1 | 12/1985 |
| GB | 2 195 808 | 4/1988 |
| GB | 2 252 656 A | 8/1992 |
| GB | 2 288 686 | 10/1995 |
| JP | 03-98080 | 4/1991 |
| WO | WO91/06935 | 5/1991 |
| WO | WO 91/11775 | 8/1991 |
| WO | WO 93/04625 | 3/1993 |
| WO | WO 93/08517 | 4/1993 |
| WO | WO 93/14483 | 7/1993 |
| WO | WO 9318475 | 9/1993 |
| WO | WO 94/25948 | 11/1994 |
| WO | WO 95/02233 | 1/1995 |
| WO | WO95/10080 | 4/1995 |
| WO | WO 95/32459 | 11/1995 |
| WO | WO 96/16389 | 5/1996 |
| WO | WO96/28800 | 9/1996 |
| WO | WO 99/38141 | 7/1999 |

OTHER PUBLICATIONS

Wierzbicki et al. Four-Dimensional Modeling of the Heart for Image Guidance of Minimally Invasive Cardiac Surgeries. Medical Imaging 2004: Visualization, Image-Guided Procedures, and Display. vol. 5367, May 2004 pp. 302-311 XP-002512099.

Gering et al. An Integrated Visualization System for Surgical Planning and Guidance Using Image Fusion and Interventional Imaging. Medical Image Computing and Computer Assisted Intervention—MICCAI' 99 Lecture Notes in Computer Science, LNCS, Springer, Berlin, DE. vol. 1679, Jan. 1, 2006 pp. 809-820 XP019036236 MIT AI Laboratory, Cambridge MA, USA Bringham & Women's Hospital, Harvard Medical School, Boston MA, USA.

Torsen Butz et al. Pre-and Intra-operative Planning and Simulation of Percutaneous Tumor Ablation Medical Image Computing and Computer Assisted Intervention Â MICCAI 2000 Lecture Notes in Computer Science, LNCS, Springer, Berlin, DE. vol. 1935, Feb. 11, 2004, pp. 317-326, XP019001272.

Nakao M et al. Haptic reproduction and interactive visualization of a beating heart for cardiovascular surgery simulation. International Journal of Medical Informatics, Elsevier Scientific Publishers, Shannon, Ireland. vol. 68, No. 1-3 Dec. 18, 2002.

Yoshitaka, Adachi et al. Intermediate Interpretation for Stiff Virtual Objects Proceedings of the Virtual Reality Annual International Symposium (VRAIS' 95) Technical Research Center, Suzuki Motor Corporation, Yokohama, Japan.

M.L. Agronin. The Design of a Nine-String Six-Degree-of-Freedom Force-Feedback Joystick for Telemanipulation. pp. 340-348 Jet Propulsion Laboratory—California, LA.

Peter K Allen et al. Acquisition and Interpretation of 3-D Sensor Data from Touch Dept. of Computer Science, Columbia University, NY CH2813-4/89/0000/0033/$01.00 1989 IEEE pp. 33-40.

Fumihito Arai et al. Intelligent Assistance in Operation of Active Catheter for Minimum Invasive Surgery. Nagoya University—Nagoya, Japan Kinjo University—Nagoya, Japan IEEE International Workshop on Robot and Human Communication 0-7803-2002-6/94 $4.00 1994 IEEE.

Daniel Bachofen et al. Enhancing the Visual Realism of Hysteroscopy Simulation Book Series: Studies in Health Technology and Informatics—Book Medicine meets Virtual Reality 14: Accelerating Change in Health Care: Next Medical Toolkit vol. 119/2005 pp. 31-36.

J. Baille et al. Use of Computer Graphics Simulation for Teaching of Flexible Sigmoidoscopy. Duke University Medical Center, North Carolina, USA. Endoscopy 3 vol. 23 May 1991 pp. 126-129.

David Baraff An Introduction to Physically Based Modeling: Ridged Body Simulation II—Nonpenetration Constraints Robotics Institute Carnegie Mellon Institute pp. 32-68 1997.

Adelstein et al. ASME Symposium 1992 Design and Implementation of a Force Reflecting Manipuladum for Manual Control Research. CA, USA.

J.H. Anderson et al. Da Vinci: A Vascular Catheterization and Interventional Radiology-Based Training and Patient Pretreatment Planning Simulator (Abstract) JVIR Supplement, Journal of Vascular and Interventional Radiology, vol. 7, No. 1, Part 2. Jan.-Feb. 1996 Washington, US.

J. Batter and F. Brooks, Jr. Grope-1: A Computer Display to the Sense of Feel 1972 North Carolina, USA.

M. Bostrom et al. Design of an Interactive Lumbar Puncture Simulator With Tactile Feedback IEEE Neutral Network Counsel Virtual Reality Annual International Symposium Conference Sep. 18-22, 1993; Seattle, Washington U.S.

M. Bostrom Design of Hardware for Simulating Lumbar Puncture with Force Feedback Thayer School of Engineering, Dartmouth College. Mar. 17, 1993.

F. P. Brooks, et al. Project Grope—Haptic Displays for Scientific Visualization ACM, Computer Graphics, vol. 24, No. 4. Aug. 1990—Chapel Hill NC, USA.

G. Burdea and T. Speeter NASA Portable Dextrous Force Feedback Master for Robot Telemanipulation (PDMFF) pp. 153-161 Technical Report Server (NTRS), NJ ,USA.

Burdea et al. A Distributed Virtual Environment with Dextrous Force Feedback Informatique '92, International Conference Interface to Real and Virtual Worlds, Rutgers University EC2 Conference Mar. 23-27, 1992, NJ, USA.

J. Capowski, Remote Manipulators as a Computer Input Device University Microfilms, a XEROX Company, Ann Arbor, Michigan UMI Dissertation Services. 1971—Michigan USA.

Cover et al. Interactively Deformable Models for Surgery Simulation (Object Modeling) Computer Graphics & Applications IEEE pp. 68-75 Atlanta, GA, USA.

J. S. Denson and S. Abrahamson A Computer-Controlled Patient Simulator Apr. 21, 1969—vol. 208, No. 3 pp. 504-508 LA, USA.

D. Gillies and C. Williams, London UK An Interactive Graphic Simulator for the Teaching of Fibrendoscopic Techniques Eurographics '87 Elsevier Science Publishers B.V North Holland pp. 127-138.

Gillies, Haritsis and Williams Computer Simulation for Teaching Endoscopic Procedures Endoscopy, Supplement II, vol. 24, Jul. 1992. pp. 455-550.

A. Haritsis D. Gillies CH. Williams (Eurographics) Realistic Generation and Real Time Animation of Images of the Human Colon Computer Graphics Forum vol. II No. 3, conference issue—Sep. 7-11, 1992. NNC Blackwell.

Haritsis 1992 (Hellenic) A.Haritsis D. Gillies CH. Williams Computer Simulation: New Horizons in Endoscopy Teaching Hellenic Journal of Gastroenterology 1992 pp. 54-63 London UK.

G. Higgins, et al. Higgins 1995 (Surg. Tech. Int'L IV) Virtual Reality Surgery: Implementation of a Coronary Angioplasty Training Simulator. University Medical Press, San Francisco, 1995. pp. 379-383.

D. Hon Ixion's Laparoscopic Surgical Skills Simulator Symposium: Medicine Meets Virtual Reality II Jan. 27-30, 1994 San Diego, USA.

D. Hon Ixion's Realistic Medical Simulations Virtual Reality World, vol. 2, No. 4 Jul. / Aug. 1994 pp. 58-62.

H. Iwata Artificial Reality with Force-feedback: Development of Desktop Virtual Space with Compact Master Manipulator. ACM SIGGRPAH 1990 Computer Graphics & Interactive Techniques vol. 24, No. 4. pp. 165-170 Aug. 6-10, 1990.

B.G Jackson L.B Rosenberg Force Feedback and Medical Simulation IOS Press and Ohmsha Jan. 19-22, 1995 pp. 147-151—CA, USA.

P.J. Kilpatrick Kilpatrick Thesis 1976 pp. 11-27 The Use of a Kinesthetic Supplement in an Interactive Graphics System. The University of North Carolina, USA.

Kotoku et al. A Force Display System for Virtual Environments and its Evaluation International Workshop on Robot and Human Communication IEEE Sep. 1-3, 1992 pp. 246-251—Ibaraki, Japan.

U.G. Kuhnapfel Realtime Graphical Computer Simulation for Endoscopic Surgery Symposium: Medicine Meets Virtual Reality II Jan. 27-30, 1994 San Diego, CA, USA.

U.G.Kuhnapfel et al. Endo surgery simulations with KISMET: a flexible tool for surgical instrument design, operation room planning and VR technology based abdominal surgery training. Virtual Reality World '95, Conference Stuttgart, Germany Computerwoche Verlag, 1995. pp. 165-171.

B. Marcus Feedback Technology and Virtual Environments pp. 87-95 Jul. 1-3, 1992—1992 International Conference on Artificial Reality and Telexistence (ICAT 1992) pp. 87-95.

Mark et al. Adding Force Feedback to Graphics Systems: Issues and Solutions Aug. 4-9, 1996 ACM SIGGRAPH 1996 Computer Graphics Proceedings, Annual Conference Chapel Hill. North Carolina, USA.

T.H. Massie Design of a Three Degree of Freedom Force-Reflecting Haptic Interface MIT, USA Thesis—pp. 6-38 May 18, 1993 Submitted May 17, 1993.

K.T. McGovern et al. The Virtual Clinic™, A Virtual Reality Surgical Simulator Symposium: Medicine Meets Virtual Reality II pp. 151-157 Jan. 27-30, 1994 San-Diego CA, USA.

D. Meglan Making Surgical Simulation Real ACM SIGGRAPH Computer Graphics pp. 37-39 Nov. 1996 Rockville, MD, USA.

Meglan et al. The Teleos Virtual Environment Toolkit for Simulation-Based Surgical Education Interactive Technology and the New Paradigm for Healthcare Proceeding of MMVR 3, IOS Press and Ohmsha pp. 346-351. Jan. 17-20, 1996 San-Diego CA, USA.

J. R. Merril The Future of Virtual Reality, Medicine, and the Information Superhighway Journal of Knowledge Engineering & Technology, vol. 7, No. 1 Spring 1994 pp. 33-35 MD, USA.

Merril et al. Photorealistic Interactive Three- Dimensional Graphics in Surgical Simulation Interactive Technology and the New Paradigm for Healthcare Proceeding of MMVR 3, IOS Press and Ohmsha pp. 244-252 Jan. 19-22, 1995 San Diego, USA.

Merril et al. Surgical Simulation Using Virtual Reality Technology: Design, Implementation, and Implications. Surgical Technology International III 1994 pp. 53-60. Published by Universal Medical Press, CA, USA.

Merril et al. Virtual Heart Surgery—Trade Show and Medical Education 1994 Virtual Reality World pp. 55-57 Jul./Aug. 1994 MD, USA.

Merril et al Cyber Surgery—Cutting Costs, Sewing Benefits The Virtual Reality Special Report, Miller Freedman Inc. Summer 1994 pp. 39-42 MD, USA.

Minsky et al. Feeling and Seeing: Issues in Force Display ACM 1990 pp. 235-243 CA, USA.

M.D. Noar N. Soehendra Endoscopy Simulation Training Devices Endoscopy 1992, vol. 24 pp. 159-166 Georg Thieme Vering Stuttgart. New York.

M.D. Noar Robotics Interactive Simulation of RCP Sphincterotomy and EGD, Endoscopy 1992, vol. 24, pp. 539-541 Supplement 2 Georg Thieme Vering Stuttgart. New York.

A. M. Noll Man-Machine Tactile Communication Polytechnic Institute of Brooklyn, Jun. 1971, pp. 1V-X111 and 1-87.

Ernest M. Otani Software Tools for Dynamic and Kinematic Modeling of Human Emotion Department of Computer & Information Science Technical Reports (CIS) University of Pennsylvania, Jul. 1989, pp. 1-74.

M. Ouh-Young Force Display in Molecular Docking UNC, The University of North Carolina at Chapel Hill 1990, pp. 1-369.

J. Peifer, et al. Medicine Meets Virtual Reality, Health Care in the Information Age Applied Virtual Reality for Simulation of Endoscopic Retrograde Cholangio-Pancreatography IOM Press, Proceedings of Medicine Meets Virtual Reality 4, San Diego, California, Jan. 17-20, 1996, pp. 36-42.

S. Pieper et al. Stereoscopic Displays and Applications II Virtual environment system for simulation of leg surgery SPIE vol. 1457, Feb. 25-27, 1991, pp. 188-197.

S. Pieper et al. Interactive Graphics for Plastic Surgery: A task-level analysis and Implementation 1992 ACM Computer Graphics Special Issue on 1992 Symposium on Interactive 3D Graphics, Cambridge, MA Mar. 29-Apr. 1, 1992, pp. 127-134.

D. Popa Simulation of Lumbar Puncture Procedure using Force Feedback in Virtual Environments Thayer School of Engineering, Dartmouth College, Hanover, New Hampshire, Jun. 1994, pp. 1-134.

Preminger et al. Medicine Meets Virtual Reality, Health Care in the Information Age Virtual Reality Surgical Simulation in Endoscopic Urologic Surgery IOM Press, Proceedings of Medicine Meets Virtual Reality 4, San Diego, California, Jan. 17-20, 1996, Chapter 19, pp. 157-163.

L.B Rosenberg, B.G Jackson Foot-Based Interfaces to Virtual Environments Using the Immersion Interface Box (TM) Virtual Reality and Persons With Disabilities, Second Annual International Conference, Jun. 8-10, 1994, pp. 145-148.

L.B Rosenberg "Virtual Fixtures"—Perceptual overlays enhance operator performance in telepresence tasks Stanford University, Aug. 1994. pp. 1-214.

M. A. Russo The Design and Implementation of a Three Degree of Freedom of Freedom Force Output Joystick MIT, May 11, 1990. pp. 1-131.

Salisbury et al. Haptic Rendering: Programming Touch Interaction with Virtual Objects Symposium on Interactive 3D Graphics, 1995 ACM, pp. 123-130.

S. S. Saliterman A Computerized Simulator for Critical-Care Training: New Technology for Medical Education Scientific session of the Mayo Medical School Alumni Society , Nov. 4, 1989, pp. 968-978.

B. Schmult et al. Application Areas for a Force-Feedback Joystick DSC vol. 49. Advances in Robotics, Mechatronics, and Haptic Interfaces ASME 1993, pp. 47-54.

Singh et al. Design of an Interactive Lumbar Puncture Simulator With Tactile Feedback IEEE International Conference on Robotics and Automation, May 8-13, 1994, pp. 1734-1739.

M. Stanley and J. Colgate Computer Simulation of Interacting Dynamic Mechanical Systems using Distributed Memory Parallel Processors ASME Winter Annual Meeting, Symposium on Haptic Interfaces for Virtual Environment and Teleoperator Systems, Nov. 8-13, 1992, pp. 55-61.

Sharon A. Stansfield Visually-Guided Haptic Object Recognition University of Pennsylvania 1987 UMI, pp. 1-216.

I. Sutherland The Ultimate Display for Production Proceedings of the IFIP Congress 1965, pp. 506-508.

D. Terzopoulos and D. Metaxas Dynamic 3D Models with Local and Global Deformations: Deformable Superquadrics . IEEE Transactions on Pattern Analysis and Machine Intelligence, vol. 13, No. 7, Aug. 30, 1990, pp. 703-714.

Williams, Baillie, Gillies, Borislow and Cotton Teaching Gastrointestinal Endoscopy by Computer Simulation: a Prototype for Colonoscopy and ERCP Gastrointestinal Endoscopy vol. 36, No. 1., 1990, pp. 49-54.

C. M. Winey III Computer Simulated Visual and Tactile Feedback as an aid to Manipulator and Vehicle Control MIT, Jul. 31, 1981, pp. 1-132.

O.C Zienkiewicz The Finite Element Method McGraw-Hill Book Company (UK) Limited, 1977, pp. 677-757.

Beth A. Marcus Hands on: Haptic Feedback in Surgical Simulation Exos, Inc., Jan. 27-30, 1994, pp. SIMB 004163-SIMB 004174.

Virtual Reality and Medicine the Cutting Edge SIG Advanced Applications, Inc. Conference and Exhibition, Sep. 8-11, 1994, The New York Hilton.

Daane et al. A $100 Surgical Simulator for the IBM PC Interactive Technology and the New Paradigm for Healthcare Jan. 1995—pp. 79-80.

Higgins U.S. Army Medical Research Grant Annual Report entitled "Medical Simulation for Trauma Management" Grant No. DAMD 17-94-J-4470.

Strutz et al. 3-D Guided Endoscopic Surgery of Paranasal Sinusese Surgical Technology International IV, Oct. 1995, pp. 195-197.

Stone Haptic Human-Computer Interaction—Haptic Feedback: A Brief History from Telepresence to Virtual Reality Haptic Human-Computer Interaction, First International Workshop, Glasgow, UK Proceedings. Aug. 31-Sep. 1, 2000.

Loftin et al. A Virtual Environment for Laparoscopic Surgical Training Medicine Meets Virtual Reality II: Interactive Technology & Healthcare, Jan. 1994.

Durrani et al. Advanced Endoscopic Imaging: 3-D Laparoscopic Endoscopy Surgical Technology International III, Oct. 1994.

Johnston et al. Assessing a Virtual Reality Surgical Skills Simulator Stud Health Technol Inform. 1996; 29:608-17.

Sheridan Automatica the Journal of IFAC the International Federation of Automatic Control / Telerobotics. Automatica, vol. 25, No. 4, pp. 487-507.

Barfield et al Virtual Environments and Advanced Interface Design 1995 pp. 358-414.

Bejczy et al. Controlling Remote Manipulators Through Kinesthetic Coupling Computers in Mechanical Engineering Jul. 1983, pp. 48-60.

Beer-Gable Computer Assisted Training in Endoscopy (C.A.T.E.): From a Simulator to a Learning Station.Endoscopy 1992; 24:suppl. 2: pp. 534-538.

Kuenhapfel et al. CAD-Based Graphical Computer Simulation in Endoscopic Surgery Institute fur Angewandte Informatik, Kernforschumgszentr urn Karlsruhe Germany, Oct. 1994.

Campos et al. A Robotic Haptic System Architecture University of Pennsylvania, Dept. of Computer & Information Science Technical Reprot No. MS-CIS-00-51 1990.

Merril et al. Changing the Focus of Surgical Training Virtual Reality World, Mar./Apr. 1995, pp. 56-60.

Szabo et al. Choreographed Instrument Movements During Laparoscopic Surgery: Needle Driving, Knot Tying, and Anastomosis Techniques. Medicine Meets Virtual Reality II; Interactive Technology & Healthcare, Jan. 1994. pp. 216-217.

Dumay Cybersurgery Medicine Meets Virtual Reality II. Interactive Technology & Healthcare, Jan. 1994.

Greenleaf DataGlove and Datasuit: Virtual Reality Technology Applied to the Measurement of Human Movement. Medicine Meets Virtual Reality II. Interactive Technology & Healthcare, Jan. 1994, pp. 63-69.

Burdea et al. Dextrous Telerobotics with Force Feedback—An Overview, Part 1: Human Factors Rutgers—The State University of New Jersey, Dept. of Electrical and Computer Engineering, Robotica (1991) vol. 9, pp. 171-178.

Online reference dated May 31, 1995, updates chapter 13 of the AutoCAD Release 13 Developer's Guide dated Apr. 14, 1995.

Brochure: Dynacath Simulator Dynacath Minneapolis, MN.

Kuhn et al. Karlsruhe Endoscopic Surgery Trainer a "Virtual Reality" based Training System for Minimally Invasive Surgery.

Christensen Bringing Telematics Into Health Care in the European Communities Medicine Meets Virtual Reality II. Interactive Technology & Healthcare, Jan. 21-23, 1994.

Marcus et al. Exos Research on Master Controllers for Robotic Devices NASA Technical Reports Server NTRS, pp. 238-245 Jan. 1, 1992.

Merril VR for Medical Training and Trade Show "Fly-Pape": Virtual Reality World, May/Jun. 1994, pp. 53-57.

Burdea Force and Touch Feedback for Virtual Reality Electrical and Computer-Engineering Dept. Rutgers—The State University of New Jersey.

Baumann et al. Force Feedback for Virtual Reality Based Minimally Invasive Surgery Simulator Medicine Meets Virtual Reality IV: Health Care in the Information Age, Jan. 1996.

Burdea Chapter 7 Force and Touch Feedback for Virtual Reality Physical Modeling, John Wiley & Sons, Inc., pp. 168-223.

Jason Fritz Rendering Techniques for Scientific Visualization Jason P. Fritz Thesis at University of Delaware Fall 1996.

Marcus Hands on: Haptic Feedback in Surgical Simulation Exos Inc. 2 A Gill St. Woburn, MA.

Rosenberg et al. A Haptic Interface for Virtual Simulation of Endoscopic Surgery Medicine Meets Virtual Reality IV: Health Care in the Information Age, Jan. 1996 pp. 371-387.

Haritsis et al. Realistic Generation and Real Time Animation of Images of the Human Colon Computer Graphics Forum, vol. II, No. 3, pp. C367-C380.

Ho et al. IGES and PDES, The Current Status of Product Data Exchange Status Dept. of Computer Science, Univ. of Mo-Rolla, Rolla MO, 1988 IEEE, pp. 210-216.

Hooper The Interactive Assembly and Computer Animation of Reconfigurable Robotic Systems Mechanical Engineering Dept. The University of Texas at Austin. 1990.

Rosenberg Louis B. Human Interface Hardware for Virtual Laparoscopic Surgery Interactive Technology and the New Paradigm for Health Care Immersion Corp. Santa Clara, CA. Chapter49, pp. 322—Jan. 1995.

Funda et al. Image-guided Command and Control of a Surgical Robot Medicine Meets Virtual Reality II. Interactive Technology & Healthcare, Jan. 1994.

Jaramaz et al. Integrating Finite Element Analysis Into Pre-Operative Surgical Planning and Simulation of Total Joint Replacement Surgery Medicine Meets Virtual Reality II. Interactive Technology & Healthcare, Jan. 1994, pp. 34-37.

Merck & Co. An Introduction to the Robotic Endoscopy Simulator 1989.

Hastreiter et al. Intuitive and Interactive Manipulation of 3D Datasets by Integrating Texture Mapping Based Volume Rendering into the Open Inventor Class Hierarchy Lehrstuhl fur Graphische Datenverarbeitung (IMMD9) Universitat Erlangen.
Issacs et al. Controlling Dynamic Simulation with Kinematic Constraints, Behavior Functions and Inverse Dynamics Computer Graphics vol. 21, No. 4, pp. 215-224.
Filerman et al. Issues in the Design of Tactile Input Devices for Mechanical CAD Systems Massachusetts Institute of Technology, Artificial Intelligence Laboratory 1989.
Artificial Reality with Force-feed back: Development of Desktop Virtual Space with Compact Master Manipulator Iwata Computer Graphics vol. 24, No. 4, pp. 165-170.
Hon Ixion's Laparoscopic Surgical Skills Simulator Medicine Meets Virtual Reality II. Interactive Technology & Healthcare, Jan. 1994.
Kilpatrick The use of a Kinesthetic Supplement in an Interactive Graphics System Xerox University Microfilms 1976.
Kuhnapfel et al. Endosurgery Simulations with KISMET Virtual Reality World, pp. 165-171 1995.
Immersion Corporation Laparoscopic Impulse Engine Impulse Engine 2000™ Software Development Kit (Ver. 1.0)(Immersion) Immersion Corporation—Version 1.0 Mar. 1995.
McKensie et al. Lasers in Surgery and Medicine Wessex Regional Medical Physics Service and Department of Otolaryngology, vol. 29, No. 6, pp. 619-641 1984.
Massie et al. The Phantom Haptic Interface: A Device for Probing Virtual Objects Proceedings of the ASME Winter Annual Meeting, Symposium on Haptic Interfaces for Virtual Environment and Teleoperator Systems, Chicago, IL Nov. 1994.
McAfee et al Teleoperator Subsystem—Telerobot Demonstrator: Force Reflecting Hand Controller Equipment Manual Jet Propulsion Laboratory, California Institute of Technology, pp. 3-11.
Poston et al. The Medical Reality Sculptor Medicine Meets Virtual Reality II. Interactive Technology & Healthcare, Jan. 1994. pp. 174-176.
Satava Medical Virtual Reality: The Current Status of the Future Medicine Meets Virtual Reality IV: Health Care in the Information Age, Jan. 1996.
Merril et al. Virtual Reality for Trade Shows and Individual Physician Training Virtual Reality Systems, pp. 40-44 Spring 2004.
Metaxas et al. Dynamic Deformation of Solid Primitives with Constraints Computer Graphics Proceedings, Annual Conference Series, University of Toronto. pp. 309-312.
Flynn Virtual Reality and Virtual Spaces Find a Niche in Real Medicine; Simulated Surgery on a Computer—This Won't Hurt. New York Times Jun. 5, 1995.
Massimo et al. One Handed Tracking in Six Degrees of Freedom IEEE International Conference on Systems, MAN and Cybernetics, Massachusetts Institute of Technology, Man-Machine Systems Laboratory, vol. 1 of III.
Hannaford et al. Performance Evaluation of a Six-Axis Generalized Force-Reflecting Teleoperator IEEE May/Jun. 1991, vol. 21, No. 3 pp. 620-633.
Merril Presentation Material: Medicine Meets Virtual Reality II. Interactive Technology & Healthcare, Jan. 1994.
Immersion Human Interface Corporation Immersion PROBE and Personal Digitizer Programmer's Technical Reference Manual: Immersion Probe and Personal Digitizer May 19, 1994.
Durlach Psychophysical Considerations in the Design of Human-Machine Interfaces for Teleoperator and Virtual-Environment Systems Medicine Meets Virtual Reality II. Interactive Technology & Healthcare, Jan. 1994 pp. 45-47.
Hubner et al. Real-Time Volume Visualization of Medical Image Data for Diagnostic and Navigational Purposes in Computer Aided Surgery Proc., Computer Assisted Radiology, CAR'96 Paris, pp. 751-756 Jun. 26-29, 1996.
Merril et al. Revealing the Mysteries of the Brain with VR Virtual Reality Special Report, Winter 1994, pp. 61-65.
Neisius et al. Robotic Telemanipulator for Laparoscopy 1995 IEEE-EMBC and CMBEC Theme 5: Neuromuscular Systems/Biomechanics, pp. 1199-1200.1995.
Sato et at. Space Interface Device for Artificial Reality—SPIDAR System and Computers in Japan, vol. 23, No. 12, pp. 44-54.

Galyean et al. Sculpting: An Interactive Volumetric Modeling Technique Computer Graphics, vol. 25, No. 4.
Medical World News Virtual Reality Shapes Surgeon's Skills Medical World News, Feb. 1994, pp. 26-27.
Hon Tactile and Visual Simulation: A Realistic Endoscopy Experience Medicine Meets Virtual Reality: Discovering Applications for 3-D Multi-Media Interactive Technology in the Health Sciences, Jun. 4-7, 1992.
Johnson Tactile Feedback Enhancement to Laparoscopic Tools Medicine Meets Virtual Reality II. Interactive Technology & Healthcare, Jan. 1994.
Fischer et al. Tactile Feedback for Endoscopic Surgery Interactive Technology and the New Paradigm for Healthcare, Jan. 1995.
Peine et al. A Tactile Sensing and Display System for Surgical Applications Interactive Technology and the New Paradigm for Healthcare, Jan. 1995 pp. 283-288.
Computer Procedures for Finite Element Analysis Taylor Computer Procedures, the Finite Element Method, McCraw Hill, pp. 677-757 Computer Procedures for Finite Element Analysis.
Hunter et al. Teleoperated Microsurgical Robot and Associated Virtual Environment Medicine Meets Virtual Reality II. Interactive Technology & Healthcare, Jan. 1994.
Holler et al. Teleprescence Systems for Application in Minimally Invasive Surgery Medicine Meets Virtual Reality II. Interactive Technology & Healthcare, Jan. 1994.
Sheridan Telerobotics Automatics vol. 25, No. 4, pp. 487-507.
Satava Virtual Reality Surgical Simulator: The First Steps Medicine Meets Virtual Reality: Discovering Applications for 3-D Multi-Media Interactive Technology in the Health Sciences—Jun. 4-7, 1992.
Frolich et al. The Responsive Workbench: A Virtual Working Environment for Physicians Interactive Technology and the New Paradigm for Healthcare, Jan. 1995, pp. 118-119.
Doyle et al. The Virtual Embryo: VR Applications in Human Developmental Anatomy Medicine Meets Virtual Reality II: Interactive Technology & Healthcare, Jan. 1994, pp. 38-41.
Bailie Gastrointestinal Endoscopy: Time for Change Scott Med J. Feb. 1989; 34 (1): 389-90.
Song et al. Tissue Cutting in Virtual Environments Interactive Technology and the New Paradigm for Healthcare, Jan. 1995.
Gyeong-Jae et al. Tissue Cutting in Virtual Environments Interactive Technology and the New Paradigm for Healthcare, Jan. 1995 359-364J.
Sukthankar Towards Virtual Reality of "Tissue Squeezing": A Feasibility Study Medicine Meets Virtual Reality II: Interactive Technology & Healthcare, Jan. 1994, pp. 182-186.
Adachi Touch and Trace on the Free-Form Surface of Virtual Object Proceedings of IEEE Virtual Reality Annual International Symposium—Sep. 18-22, 1993 Seattle, WA pp. 162-168.
Trevidi et al. Developing Sensor-Based Robotic System-Using Virtual Reality Concepts Proceedings for the ANS Fifth Topical Meeting on Robotics and Robotic Systems Knoxsville, TN/Apr. 25-30, vol. 1, pp. 165-172.
CH Products CH Products Virtual Pilot Control Yoke 1993.
Henderson "Virtual Realities" as Instructional Technology Journal of Interactive Instruction Development, pp. 24-30.
Hoffman Virtual Reality and the Medical Curriculum: Integrating Extant and Emerging Technologies Medicine Meets Virtual Reality II: Interactive Technology & Healthcare, Jan. 1994 pp. 73-76.
Burdea et al. Virtual Reality Technology Chap. 6, pp. 221-242. Wiley-Interscience 2003.
Iwata et al. Volume Haptization IEEE 1993, pp. 16-18.
Anon. VR in Medicine VR News; Apr. 1996 vol. 5, Issue 3.
Ota et al. Virtual Reality in Surgical Education ComputBiol Med., Mar. 1995, 25(2): 127-37.
MacDonald et al. Virtual Reality Technology Applied to Anesthesiology Interactive Technology and the New Paradigm for Healthcare, Jan. 1995.
Bell et al. The Virtual Reality Modeling Language, version 1.0 Specification 1996.
Merril Why I Simulate Surgery . . . Virtual Reality World, Nov./Dec. 1994, pp. 54-57.
Levy, "Constrained Texture Mapping for Polygonal Meshes", ACM SIGGRAPH, Aug. 12-17, 2001, Los Angeles, CA, pp. 417-424.

Vidal, "Simulation of Image Guided Needle Puncture: Contribution to Real-time Ultrasound and Fluoroscopic Rendering, and Volume Haptic Rendering", School of Computer Science, Bangor University, United Kingdom Jan. 1, 2008, pp. 1-230.

Office Action issued by the United States Patent and Trademark Office for U.S. Appl. No. 12/405,954 dated Jun. 11, 2012.

Office Action issued by the United States Patent and Trademark Office for U.S. Appl. No. 13/015,343 dated Jun. 7, 2012.

Zeman et al., "Prototype Vein Contrast Enhancer", Advanced Biomedical and Clinical Diagnostic Systems II, Proceedings of SPIE vol. 5318, Dec. 31, 2004, pp. 39-49.

Office Action issued by the United States Patent and Trademark Office for U.S. Appl. No. 12/405,954 dated Jan. 4, 2013.

* cited by examiner

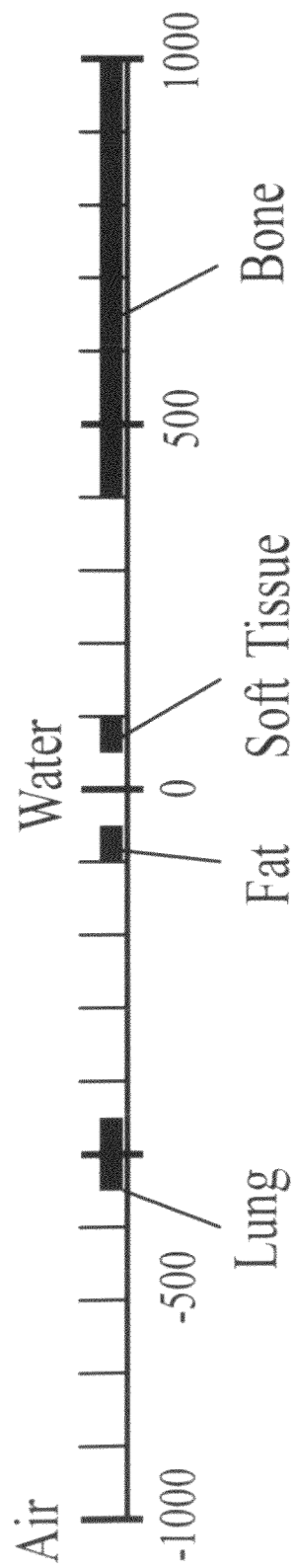
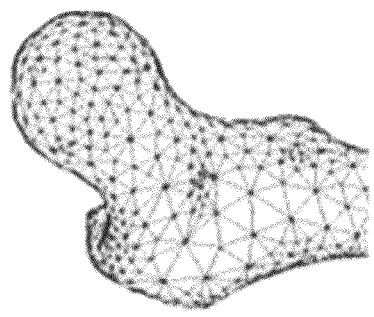
Fig. 2C
Fig. 2A
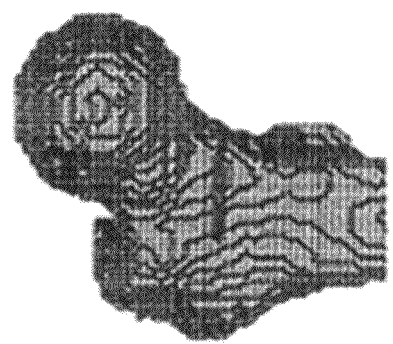
Fig. 2B

PREOPERATIVE SURGICAL SIMULATION

RELATED APPLICATIONS

This Application is a National Phase of PCT Patent Application No. PCT/IL2008/000056 having International filing date of Jan. 13, 2008, which claims the benefit of U.S. Provisional Patent Application No. 60/880,415 filed on Jan. 16, 2007. The contents of the above applications are all incorporated herein by reference.

FIELD AND BACKGROUND OF THE INVENTION

The present invention relates to an apparatus and a method for performing a simulated image-guided medical procedure and, more particularly, but not exclusively to performing a simulated image-guided procedure according to a three-dimensional (3D) model of an organ that is based on a 3D medical image.

Medical imaging is generally recognized as important for diagnosis and patient care with the goal of improving treatment outcomes. In recent years, medical imaging has experienced an explosive growth due to advances in imaging modalities such as x-rays, computed tomography (CT), magnetic resonance imaging (MRI) and ultrasound. These modalities provide noninvasive methods for studying internal organs in vivo, but the amount of data is relatively large and when presented as two dimensional (2D) images, it generally requires an anatomist/radiology specialist for interpretation. Unfortunately, the cost incurred in manual interpretation of this data is prohibitive for routine data analysis. The 2D slices can be combined to generate a 3-D volumetric model.

Such medical imaging systems allow the performance of minimally invasive therapeutic procedures. These procedures are typically carried out in a CathLab, where a physician wishes to assess the functions of internal organ such as the heart and coronary artery or to perform procedures such as coronary angioplasty.

Most radiology yields recorded images such as 2D X-ray films or 3D medical images such as CT and MRI scans. Mild dosage interactively controlled X-Ray, also known as fluoroscopy, allows a physician to monitor actively an operation at progress. Interventional radiology is the specialty in which the radiologist and cardiologists utilizes real time radiological images to perform therapeutic and diagnostic procedures. Interventional radiologists currently rely on the real-time fluoroscopic 2D images, available as analog video or digital information viewed on video monitors.

However, these procedures involve delicate and coordinated hand movements, spatially unrelated to the view on a video monitor of the remotely controlled surgical instruments. Depth perception is lacking on the flat video display and therefore it is not an easy task to learn to control the tools through the spatially arbitrary linkage. A mistake in this difficult environment can be dangerous. Therefore, a high level of skill is required, and a realistic training of these specialists is a complex task. In addition, usually there is no direct engagement of the depth perception of the radiologist, who must make assumptions about the patient's anatomy to deliver therapy and assess the results.

Medical simulators that can be used to train such medical specialists have significant potential in reducing healthcare costs through improved training, better pre-treatment planning, and more economic and rapid development of new medical devices. Hands-on experience becomes possible in training, before direct patient involvement that will carry a significant risk.

Image-guided procedures, such as vascular catheterization, angioplasty, and stent placement, are specially suited for simulation because they typically place the physician at-a-distance from the operative site manipulating surgical instruments and viewing the procedures on video monitors.

For example, U.S. Pat. No. 6,062,866 published on May 16, 2000 describes a medical model for teaching and demonstrating invasive medical procedures such as angioplasty. The model is a plastic, transparent three-dimensional, anatomically correct representation of at least a portion of the vascular system and in a preferred embodiment would include the aorta, coronary artery, subclavian arteries, pulmonary artery and renal arteries each defining a passageway or lumen. An access port is provided so that actual medical devices, such as a guide and catheter may be inserted to the location-simulated blockage. Fluid may also be introduced to simulate realistically in vivo conditions. Simulated heart chambers of similar construction may also be attached to the aortic valve to enhance further the representation of invasive procedures.

More complex simulation systems that provide more accurate, linked visual and tactile feedback during the training is disclosed in U.S. patent application No. 2003/0069719 published Apr. 10, 2003 that describes an interface device and method for interfacing instruments to a vascular access simulation system serve to interface peripherals in the form of mock or actual medical instruments to the simulation system to enable simulation of medical procedures. The interface device includes a catheter unit assembly for receiving a catheter needle assembly, and a skin traction mechanism to simulate placing skin in traction or manipulating other anatomical sites for performing a medical procedure. The catheter needle assembly and skin traction mechanism are manipulated by a user during a medical procedure. The catheter unit assembly includes a base, a housing, a bearing assembly and a shaft that receives the catheter needle assembly. The bearing assembly enables translation of the catheter needle assembly, and includes bearings that enable the shaft to translate in accordance with manipulation of the catheter needle assembly. The shaft typically includes an encoder to measure translational motion of a needle of the catheter needle assembly, while the interface device further includes encoders to measure manipulation of the catheter needle assembly in various degrees of freedom and the skin traction mechanism. The simulation system receives measurements from the interface device encoders and updates the simulation and display, while providing control signals to the force feedback device to enable application of force feedback to the catheter needle assembly.

Another example for a simulating system that is designed to simulate an image guiding procedure according to a predefined and fixed module is disclosed in U.S. Pat. No. 6,538,634 published on Mar. 25, 2003.

These simulation systems and other known simulation systems are based on predefined models, which are acquired and enhanced before the systems become operational or during a maintenance thereof, such as updating the system. Usually, a library that comprises virtual models which are stored in a related database is connected to the simulation system. During the operational mode, the system simulates an image-guided procedure according to one of the virtual models that has been selected by the system user.

Though such systems allow physicians and trainees to simulate image-guided procedures, the simulated image-guided procedures are modeled according to predefined or randomly changed models of an organ, a human body system, or a section thereof. As such, the physician or the trainee is trained using a model of a virtual organ that is not identical to the organ that he or she is about to perform an operative image-guided procedure on.

Moreover, when a virtual model is used, the simulation system cannot be used for accurately simulating an operation that has been performed on a real patient. Therefore, the currently used simulation systems cannot be used for going back over an operation that went wrong or for didactic purposes.

There is thus a widely recognized need for, and it would be highly advantageous to have, a system for simulating image-guided procedures, devoid of the above limitations, that can simulate in a more realistic manner the image-guided procedure that the physician is about to perform.

SUMMARY OF THE INVENTION

According to one aspect of the present invention there is provided an apparatus for simulating an image-guided procedure. The apparatus comprises an input for receiving a three-dimensional (3D) medical image depicting an organ of a patient, a model generation unit configured for generating a 3D anatomical model of the organ according to the 3D medical image, and a simulating unit configured for simulating an image-guided procedure planned for the patient according to the 3D anatomical model.

Preferably, the apparatus further comprises a segmentation unit operatively connected to the model generation unit, the segmentation unit being configured for segmenting the organ in the 3D medical image to a plurality of areas, the segmented organ image being used for generating the 3D anatomical model.

Preferably, the 3D anatomical model is a model of a tract.

More preferably, the tract is a member of the following group: a vascular tract, a urinary tract, a gastrointestinal tract, and a fistula tract.

Preferably, the 3D medical image is a member of the following group: computerized tomography (CT) scan images, magnetic resonance imager (MRI) scan images, ultrasound scan images, and positron emission tomography (PET)-CT scan images.

Preferably, the planned image-guided procedure is an angioplasty procedure.

Preferably, the apparatus further comprises a user interface operatively connected to the model generation unit, the user interface allows a user to instruct the model generation unit during the generation of the 3D anatomical model.

Preferably, the simulated planned image-guided procedure is used as a study case during a learning process.

Preferably, the simulated planned image-guided procedure is used to demonstrate a respective image-guided procedure to the patient.

Preferably, the simulated planned image-guided procedure is used to document preparation to an operation.

Preferably, the input is configured for receiving a four dimensional (4D) medical image depicting the organ during a certain period, the model generation unit configured for generating a 4D organ model of the organ according to the 4D medical image, the simulating unit configured for simulating an image-guided procedure planned for the patient according to the 4D organ model.

Preferably, the organ is a member of a group comprising: an anatomical region, a human body system, an area of an organ, a number of areas of an organ, a section of an organ, and a section of a human body system.

According to one aspect of the present invention there is provided a method for performing a simulated image-guided procedure. The method comprises the following steps: a) obtaining a three-dimensional (3D) medical image depicting an organ of a patient, b) producing a 3D anatomical model of the organ according to the 3D medical image, and c) simulating an image-guided procedure planned for the patient according to the 3D model.

Preferably, the method further comprises a step a1) between step a) and b) of segmenting the organ in the 3D medical image to a plurality of areas, the producing of step b) is performed according to the segmented 3D medical image.

Preferably, the planned image-guided procedure is an angioplasty procedure.

Preferably, the producing comprises a step of receiving generation instructions from a system user, the generation instructions being used for defining the 3D model.

Preferably, the simulating comprises displaying the organ.

More preferably, the method further comprises a step of allowing a system user to mark labels for the planned image-guided procedure according to the display.

Preferably, the planned image-guided procedure is an angioplasty procedure.

Preferably, the simulation is a pre-operative surgical simulation.

Preferably, the 3D anatomical model is a model of a tract.

Preferably, the 3D anatomical model is a tract model.

More preferably, the tract model define a member of the following group: a vascular tract, a urinary tract, a gastrointestinal tract, and a fistula tract.

Preferably, the obtaining comprises a step of obtaining a four dimensional (4D) medical image depicting the organ during a certain period, the producing comprises a step of producing a 4D model of the organ according to the 4D medical image, the simulating is performed according to the 4D model.

Preferably, the organ is a member of a group comprising: an anatomical region, a human body system, an area of an organ, a number of areas of an organ, a section of an organ, and a section of a human body system.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2A is a graphical representation of the Hounsfield scale, which measures attenuation of X-Ray radiation by a medium. Hounsfield values of different human tissues are marked;

FIGS. 2B and 2C respectively illustrate schematically two triangular surface models of a femur bone, one directly generated from scan data, and a coarsened variant of the segment in FIG. 2B which is generated according to one preferred embodiment of the present invention;

DESCRIPTION OF THE PREFERRED EMBODIMENTS

Figure 1:
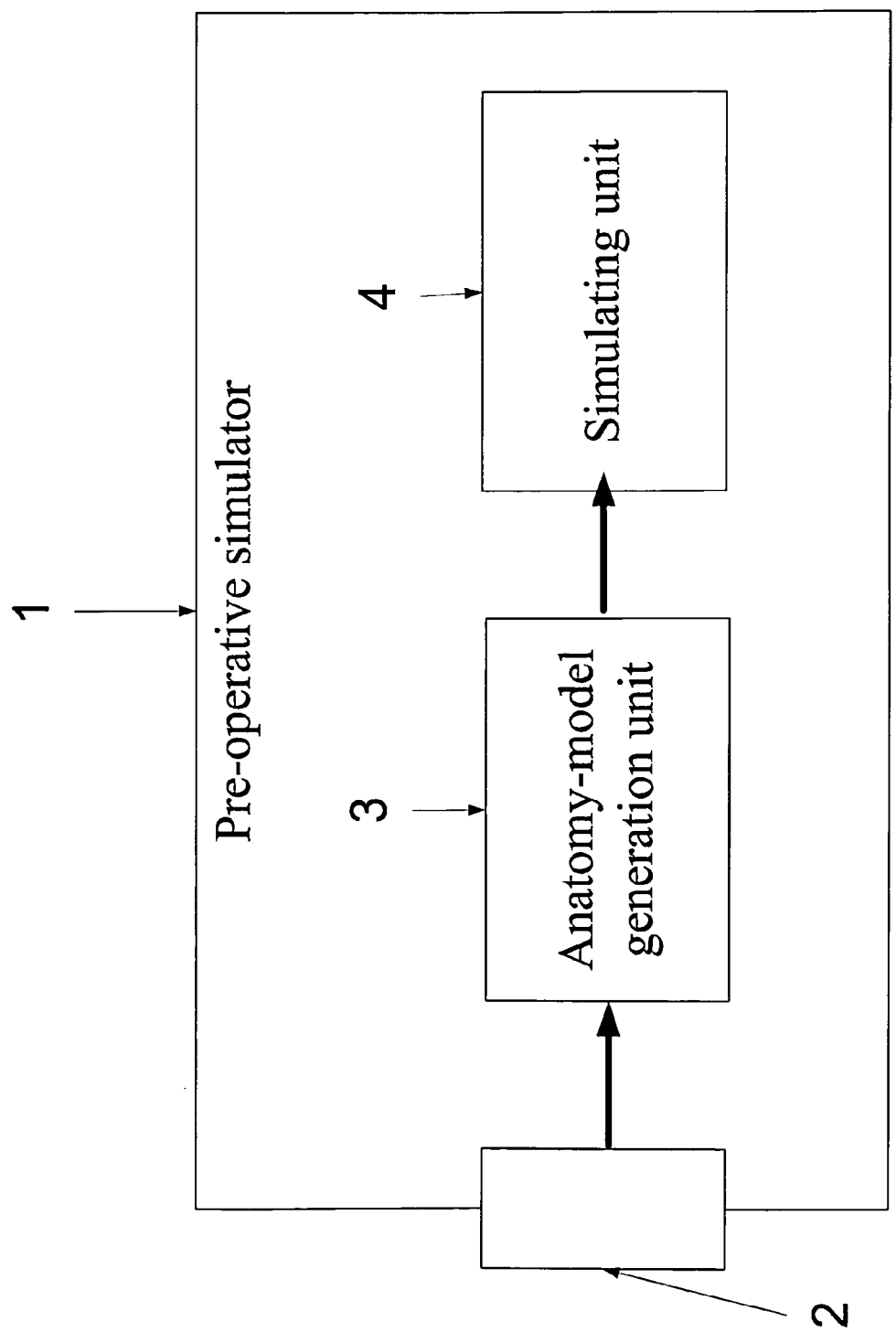
FIG. 1 is a schematic representation of a pre-operative simulator for simulating an image-guided procedure, according to one preferred embodiment of the present invention.

The present embodiments comprise a apparatus and a method for simulating an image-guided procedure. According to one embodiment of the present invention, the apparatus and the method allow a physician to set a pre-operative simulation of an image-guided procedure. The pre-operative simulation simulates an image-guided procedure that is about to be performed on a certain patient. In order to allow such a case-specific simulation, a 3D medical image that depicts an anatomical region of a certain patient who is about to be operated on is acquired and 3D anatomical models are generated based thereupon. Preferably, the 3D anatomical model defines the boundaries of a certain anatomy or an organ such as a vascular tract. During the pre-operative simulation, the 3D anatomical models are used for simulating an image-guided procedure on that region.

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

A 3D medical image may be understood as a sequence of CT scan images, a sequence of MRI scan images, a sequence of PET-CT scan images, a spatial image, etc.

A medical imaging system may be understood as an MRI imaging system, a CT imaging system, a PET-CT imaging system, etc.

An organ or an anatomical region may be understood as human body organ, a human body system, an area of an organ, a number of areas of an organ, a section of an organ, a section of a human body system, etc.

Reference is now made to FIG. 1, which is a schematic representation of a pre-operative simulator 1 for simulating an image-guided procedure, according to one preferred embodiment of the present invention. The pre-operative simulator 1 comprises an input unit 2 for obtaining a 3D medical image that depicts an anatomy region of a patient and an anatomy-model generation unit 3 that is designed for generating a 3D anatomical model of an organ according to the received 3D medical image. The pre-operative simulator 1 further comprises a simulating unit 4 for simulating an image-guided procedure according to the three-dimensional model, as described below.

The input unit 2 preferably allows the system for simulating image-guided procedure 1 to fetch the 3D medical image from a medical images server such as a picture archiving communication system (PACS) before being accessed by the physicians. The PACS server comprises a number of computers, which are dedicated for storing, retrieving, distributing and presenting the stored 3D medical images. The 3D medical images are stored in a number of formats. The most common format for image storage is digital imaging and communications in medicine (DICOM). Preferably, the fetched 3D medical image is represented in a 3D array, preferably of 512·512·150 voxels.

In one embodiment, the input unit 2 receives as input a raw 3D data array, composed as a pre-fetched and pre-parsed DICOM image. The segmentation is not limited to a specific modality. Preferably, the 3D medical image is a CT scan. In such an embodiment, each voxel is represented by a single measured value, physically corresponding to the degree of X-ray attenuation of a respective location in the depicted organ. Preferably, the data acquisition modality is CT-angiography (CTA).

The input unit 2 may be adjusted to receive the 3D medical image from a PACS workstation, a computer network, or a portable memory device such as a DVD, a CD, a memory card, etc.

The received 3D medical image is forwarded to the anatomy-model generation unit 3 that is designed for generating the 3D anatomical model, as described above. Preferably, the anatomy-model generation unit 3 comprises a 3D image segmentation unit that is used for segmenting the received 3D medical image into anatomical structures. The segmentation is performed either automatically or semi-automatically. In one embodiment, a standard automatic segmentation procedure is used for segmenting the image.

Preferably, the segmentation is based on a procedure in which relevant voxels of the received raw 3D data array are isolated. For example, if the raw 3D data array is based on a CT scan, the physical attenuation is scaled in HUs, where the value −1000 HU is associated with air and the value 0HU is associated with water, as shown at FIG. 2A. On such a scale, different tissue types have different typical HU ranges. The typical attenuation of a specific tissue is used to isolate it in a 3D array of CT data. For example, the value of voxels that depict lungs is usually between −550 HU and −450 HU and the value of voxels that depict bones is approximately between 450 HU and 1000 HU.

In such an embodiment, the HU values of voxels of the 3D medical image are used for isolating the voxels in the tissue of interest. Preferably, in order to improve precision of the segmentation procedure, intravenous contrast enhancement (ICE) components, such as Barium, Iodine or any other radiopharmaceutical component, are applied when the 3D medical image is taken. The ICE components increase the HU value of blood vessels to the HU value of bones and sometimes beyond. Such an increment results in a higher contrast between the vessel voxels and the surrounding that can improve the segmentation procedure. Preferably, the segmentation procedure is adapted to segment a subset of scanned voxels from the 3D medical image, wherein the stored values of the voxels in the subset is in a predefined range. In one embodiment, all the voxels with stored values in the range of blood vessels is segmented and tagged.

In one embodiment of the present invention, a triangle mesh is computed from the raw 3D data array of the HU values. Preferably, a variant of the marching cubes algorithm is used for initial generating the triangle mesh, see Marching Cubes: "A High Resolution 3D Surface Construction Algorithm", William E. Lorensen and Harvey E. Cline, Computer Graphics (Proceedings of SIGGRAPH '87), Vol. 21, No. 4, pp. 163-169. The triangle mesh is used for surface construction of segments in the 3D medical image. The mesh obtained by the variant of the marching cube algorithm bounds the desired volume of the segment. As the segment is obtained in the resolution of the 3D medical image, it may be extremely fine. Therefore, preferably, an additional decimation processing stage is carried out, in which the mesh is coarsened and the level of surface approximation of the segments is reduced.

Preferably, an Edge-Collapse operation is used for the coarsening, see Hoppe, H. Progressive meshes. In Proc. SIGGRAPH '96, pages 99-108, August 1996 and Hussain, M., Okada, Y. and Niijima, K. Fast, simple, feature-preserving and memory efficient simplification of triangle meshes. International Journal of Image and Graphics, 3(4):1-18, 2003. An example for such decimation is depicted in FIGS. 2B and 2C that respectively depict a schematic illustration a segmented femur bone and a coarsened variant of the segmented femur bone that has been generated by applying the aforementioned decimation processing. Preferably, the 3D medical image is represented in a 3D array. of 512×512×150, wherein each voxel is preferably represented by a value in one of the following formats: 8-bit (1 byte storage), 12-bit (2 byte storage), 16 bit (2 byte storage), and a single-precision floating point (4 byte storage).

Preferably, the segmentation procedure is adapted to segment the anatomy that is depicted in the received 3D medical image. Different anatomic parts have different characteristics that affect segmentation.

During the image-guided procedures, a catheter or the like is conveyed by a physician via a certain tract. Therefore, the segmentation procedure's object is to identify such a tract and to segment it or to segment all the areas that delimit that tract.

For example, if the received 3D medical image depicts a cervical portion of the human spine and the image-guided procedure is an angioplasty procedure, such as carotid stenting, the carotid artery is the tract through which the catheter or alike is conveyed. In such a case, the carotid artery should be segmented. The artery net possesses a-priori known traits that can be exploited to enhance and verify the fidelity of the segmentation stage. For example, if the area is a cervical portion and the procedure is carotid stenting, the following anatomical structures are exploited: the thoracic aorta, the brachiocephalic trunk, the Subclavian arteries, the carotid arteries, and the vertebral arteries.

Preferably, blood vessels in the image of the organ are identified and segmented during the segmentation procedure. Preferably, during the segmentation the centerline, the radius and the inter-connectivity of each one of the main blood vessels in the image are identified and registered.

Preferably, the anatomy-model generation unit 3 is connected to a user interface (not shown). In such an embodiment, a simulator user may be asked, for example, to mark one or more points on a depicted tract. For example, if the received 3D medical image depicts a cervical portion of the human spine and the image-guided procedure is an angioplasty procedure, the simulator user may be required to mark the left carotid artery as a starting point for the automatic segmentation.

When the segmentation process is completed, a segmented version of the 3D image or an array that represents the segmented areas and the tracts is generated. The segmented areas can be represented in several formats and sets of data. Preferably, the segmented 3D image is represented by using one or more of the following sets of data:

a. A cubic Catmull-Rom 3D spline description of a central curve of each artery or any other tract portion;

b. A tree description, graph description or any other description that describes the connectivity between arteries or any other tract portions. For example, such a description describes in which point an artery X emanates an artery Y;

c. A cubic Catmull-Rom 2D spline description of the radius of each artery at each point on its central curve;

d. A triangular surface mesh that describes the surface of the vasculature anatomy;

e. Polygonal meshes describing other organs captured in the scan—Lungs, heart, kidneys, etc; and f. Classification of each raw data voxel to its designated part of anatomy (a vessel voxel, a kidney voxel, etc.).

The segmented 3D medical image or an array representing segments in the 3D medical image is forwarded to the simulating unit 4.

It should be noted that the pre-operative simulator 1 may also be used to simulate an image-guided procedure according to a four dimensional (4D) image, which is a set of 3D medical image that depicts a certain organ during a certain period. In such an embodiment, a 4D image is received by the input 2. The received 4D medical image is forwarded to the anatomy-model generation unit 3 that is designed for generating the 4D model. Preferably, the anatomy-model generation unit 3 comprises a 4D image segmentation unit that is used for segmenting the received 4D medical image into anatomical structures. The segmentation is performed either automatically or semi-automatically. In one embodiment, each one of the 3D medical image that comprise the received 4D medical image is separately segmented, as described below.

Figure 3:
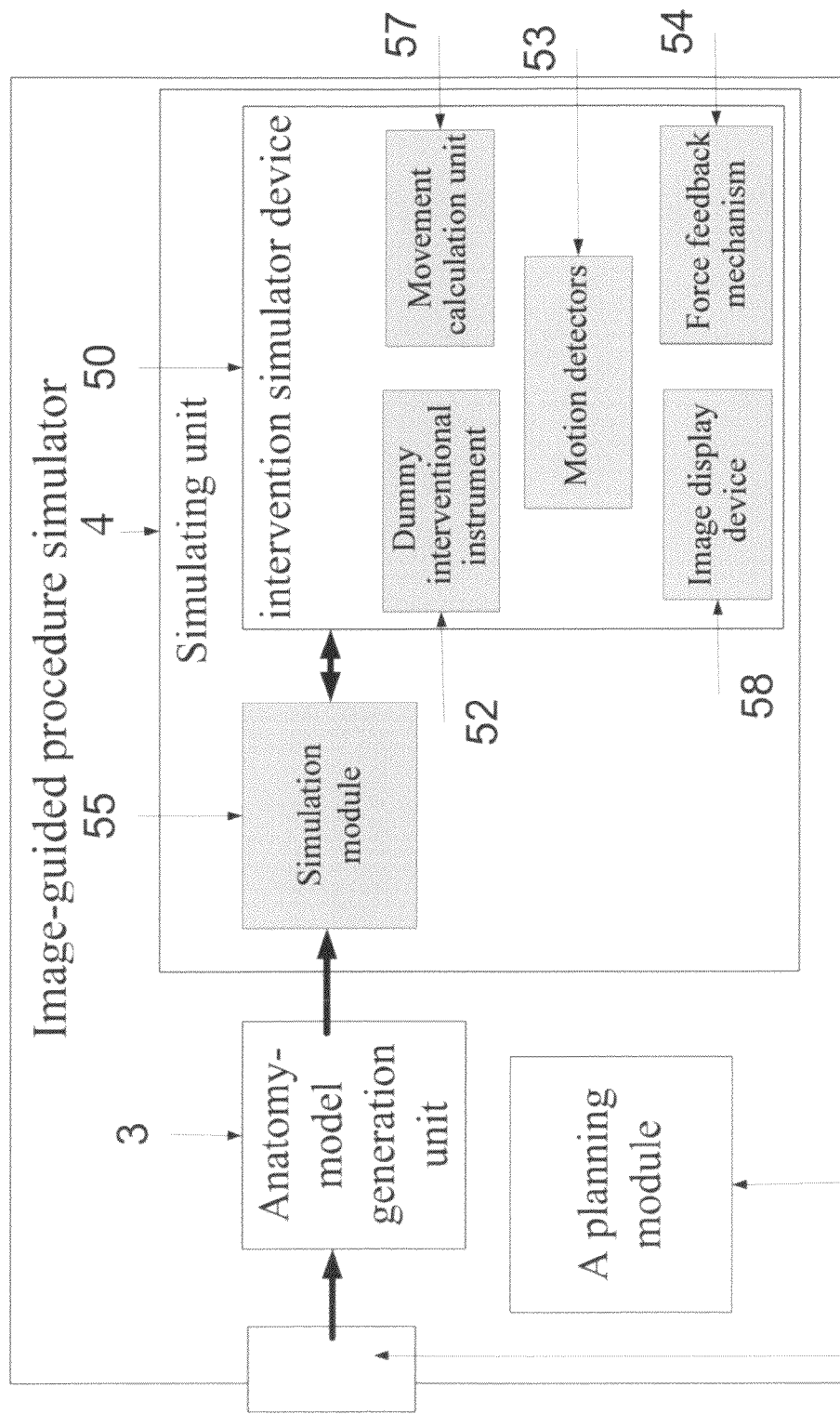
FIG. 3 is a schematic representation of the pre-operative simulator of FIG. 1 with a detailed description of the simulating unit, according to one embodiment of the present invention.

Reference is now made to FIG. 3, which is a block diagram representing the pre-operative simulator 1, which is depicted in FIG. 1, the components of the simulating unit 4, and a planning module 51, according to one embodiment of the present invention.

The simulating unit 4 preferably comprises two subsystems. The first subsystem is an intervention simulator device 50 constituted by a dummy interventional instrument 52, motion detectors 53, a movement calculation unit 57, an image display device 58, and a force feedback mechanism 54. The second subsystem is a simulation module 55 that has the functions of receiving inputs from the motion detectors 53, analyzing the inputs using the movement calculation unit 57, translating the outcome to visual and tactile outputs and transferring them to the display device 58 and to the force feedback mechanism 54. The simulation module 55 has also the functions of receiving the segmented 3D medical image from the anatomy-model generation unit 3, wherein the received segmented 3D medical image is already translated to a 3D model that simulates the organ that is depicted in the segmented 3D medical image. As described above the segmented 3D medical image is based on a 3D medical image that is received from the actual patient who is about to be operated on.

Figure 4:
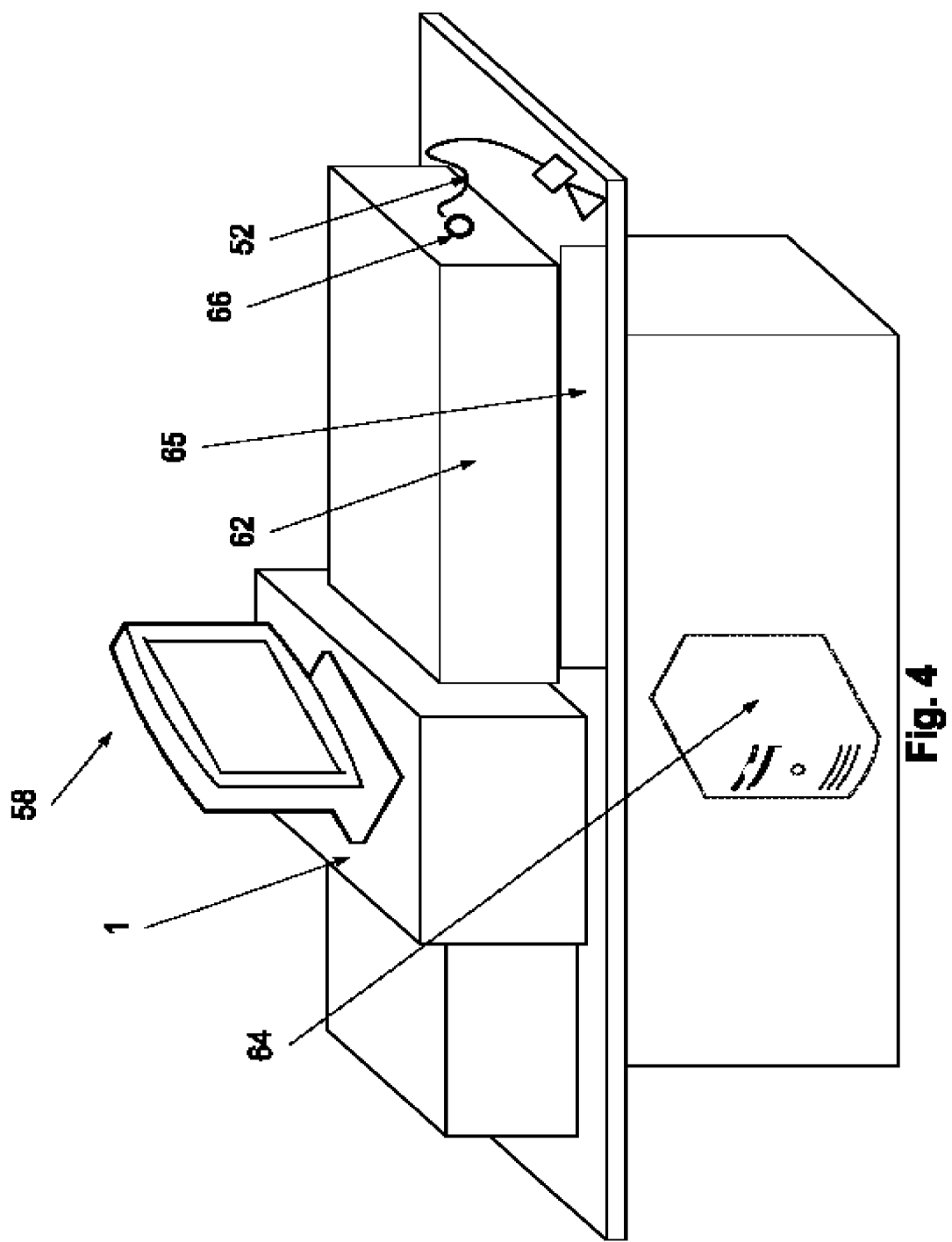
FIG. 4 is an exemplary illustration of the pre-operative simulator of FIG. 3, according to an embodiment of the present invention.

Reference in now made to FIG. 4, which is an exemplary illustration of the aforementioned pre-operative simulator 1 for simulation of an image-guided procedure according to an embodiment of the present invention. The dummy intervention instrument 52 and the image display device are as in FIG. 3, however FIG. 4 further depicts an enclosure 62, a computer processor 64, and a user input interface 65. In use, a physician prepares himself for the operative image-guided procedure by manipulating the dummy interventional instrument 52 that is preferably a dummy catheter. The dummy interventional instrument 52 is inserted into a cavity 66 within an enclosure 62 that comprises the motion detectors and force feedback components (not shown), such as resisting force generators, of the force feedback mechanism (not shown). As the physician manipulates the dummy interventional instrument 52, tactile and visual feedbacks are determined according to the position of dummy interventional instrument 52 within the enclosure 62 in respect to the aforementioned 3D model of the simulated organ. Visual feedback is provided in the form of a display on the image display device 58 and tactile feedback is provided from the force feedback components within the enclosure 62. The visual and tactile feedbacks, which are respectively displayed on the image display device 58 and imparted on the dummy interventional instrument 52 are designed to improve technical and operational skills of the physician. The visual feedback is given by a display device 58 that displays a sequence of consecutive images, which are based on a 3D model that is based on the received 3D medical image. The tactile feedback is given by imparting different pressures on the dummy interventional instrument respective to the movement signals as received from the imaging simulation module, in respect to the 3D model that is based on the received 3D medical image. The different pressures simulate the actual tactile feeling the physician experiences during a real image-guided procedure and reflects the actual reaction of the patient tissues to the dummy interventional instrument 52 manipulation.

The image display device 58 displays a real time feedback image as transferred from the simulation module (not shown). The real time feedback image represents a visual image as seen if an interventional instrument was inserted into the organ of the patient which is about to be operated on. The visual image is an accurate and realistic simulation of the visual data that would be received from the related organ.

Preferably, the simulation module and the anatomy-model generation unit 3 are supported by a processor such as an Intel Pentium Core-Duo, with an nVidia GeForce-6+(6600 onwards) GPU.

Figure 5:
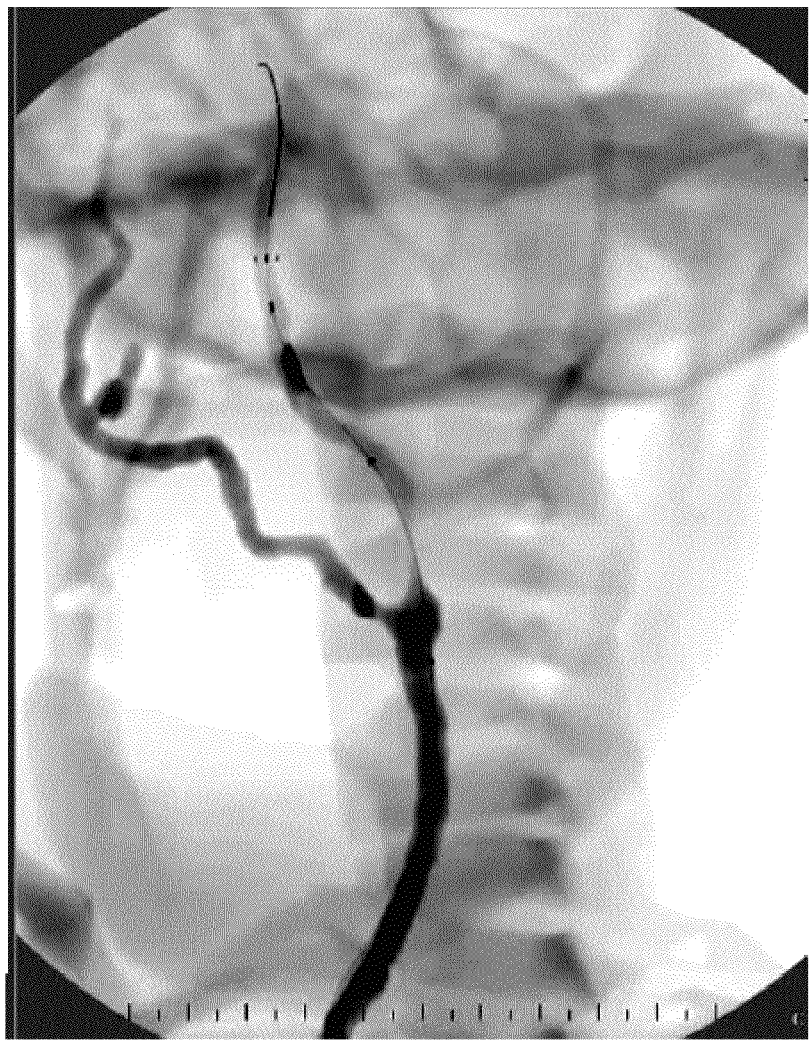
FIG. 5 is an exemplary illustration of a screen display taken during the simulation of an image-guide procedure, according to an embodiment of the present invention.

Reference is now made, once again, to FIG. 3. The simulation module 55, through the processor, is utilized to prepare simulated organ visual images as displayed on the screen during the operative image-guided procedure. The visual feedback is rendered for simulating a visual display of the organ during the simulated image-guided procedure, as shown in FIG. 5 that is a simulated fluoroscopic image of Carotid stenting. Preferably, the simulation module 55 simulates a number of vascular tracts, according to the received 3D medical image. At the same time, the simulation module 55 receives navigation signals from the motion detectors 53, which are located along the enclosure cavity. The simulation module 55 uses the processor to calculate the position of the dummy interventional instrument 52 within the enclosure cavity according to the navigation signals and updates the visual image of the organ, as described above, with the instantaneous respective position of the dummy interventional instrument 52. Moreover, the simulation module 55 simulates realistic interaction between the simulated instrument, such as a catheter, and the simulated anatomy, including—but not limited to—catheter twist and bend, vessel flexing and optionally vessel rupture.

In addition, and in correspondence with the visual information, the simulation module 55 also instructs the components of the force feedback 54 to impart pressure on the dummy interventional instrument 52 in a manner that simulates the instantaneous tactile feedback of the procedure. Such visual images and tactile feedback simulate the actual feedback as received during an actual medical procedure as performed on an actual subject and therefore reflect to the physician the current location and bending of the interventional instrument along the simulated organ. Clearly, the pre-operative simulator 1 is not bound to the simulation of a particular organ, such as a vascular tract, but can reflect a visual display of various elements and organs relative to the instantaneous position of the interventional instrument. Simulators of image-guided procedures are not described here in greater detail as they are generally well known and already comprehensibly described in the incorporated patents and in publications known to the skilled in the art.

The pre-operative simulator 1 is designed to allow a physician to conduct a pre-operative surgical simulation of the image-guided procedure he or she is about to perform on a certain patient. In such an embodiment, the physician refers the certain patient to a medical imaging system for acquiring a 3D medical image of an organ that is about to be operated on. The acquired 3D medical image is then forwarded to the PACS server. Later on, the acquired 3D medical image is obtained by the pre-operative simulator 1 from the PACS server. The 3D medical image is used as the basis for a 3D anatomical model of the organ. The 3D anatomical model is generated by a segmentation unit that is designed for segmenting the organ into a number of areas, as described in greater detail above.

It should be noted that such a pre-operative simulator 1 can also be used for explaining and demonstrating to the patient the details of his pathology and the operation he is about to undergo.

In one embodiment of the present invention, the pre-operative simulator 1 can also be used as a learning tool. Known simulators are designed to simulate an image-guided procedure on a predefined model of a virtual organ. As the simulated organ is a virtual organ, the trainer cannot be experienced in diagnosing a real patient in a manner that allows him to receive a more comprehensive overview of the related case. As opposed to that, the pre-operative simulator 1 allows the performance of patient-specific simulations of real anatomy, as described above. As such, the pre-operative simulator 1 can be used for teaching a very real case, with real anatomy, lesions, problems, conflicts and resolutions. Physicians can experience a more realistic image-guided procedure, and decisions may be taken during the simulated image-guided procedure based on the overall medical history and the medical condition of the patient himself.

In one embodiment of the present invention, the pre-operative simulator 1 can also be used as a planning tool. The planning module 51, which is depicted in FIG. 3, is preferably connected to the image display device 58 or to any other display device and to a user interface. The planning module 51 supports tools for allowing physicians to plan an operative image-guided procedure according to the aforementioned case-specific simulation. The module preferably allows the physician to sketch and to take notes during the image-guided procedure simulation. Preferably, the image display device 58 is a touch screen that allows the physician to sketch a track that depicts the maneuvers that he intends to take during the operative image-guided medical procedure. Moreover, in such an embodiment, the physician can mark problematic areas of the depicted organ. In one preferred embodiment, the image-guided procedure simulation is an angioplasty procedure simulation. The physician can use the touch screen to sketch the boundaries of the tract through which he intends to perform the procedure or a portion thereof.

In one embodiment of the present invention, the pre-operative simulator 1 can also be used as an analyzer tool for going back over performed operations. As described above, the model of the operated organ is generated according to a medical image of an organ which is about to be operated. In one embodiment of the present invention the pre-operative simulator 1 is used for performing a reenactment of the image-guided procedure that has been performed on the patient. Such a reenactment is performed as an image-guided procedure simulation, as described above. As the model that is used by the pre-operative simulator 1 simulates the operated on organ, the reenactment is realistic and allows the physicians to be prepared better to the operation.

Figure 6:
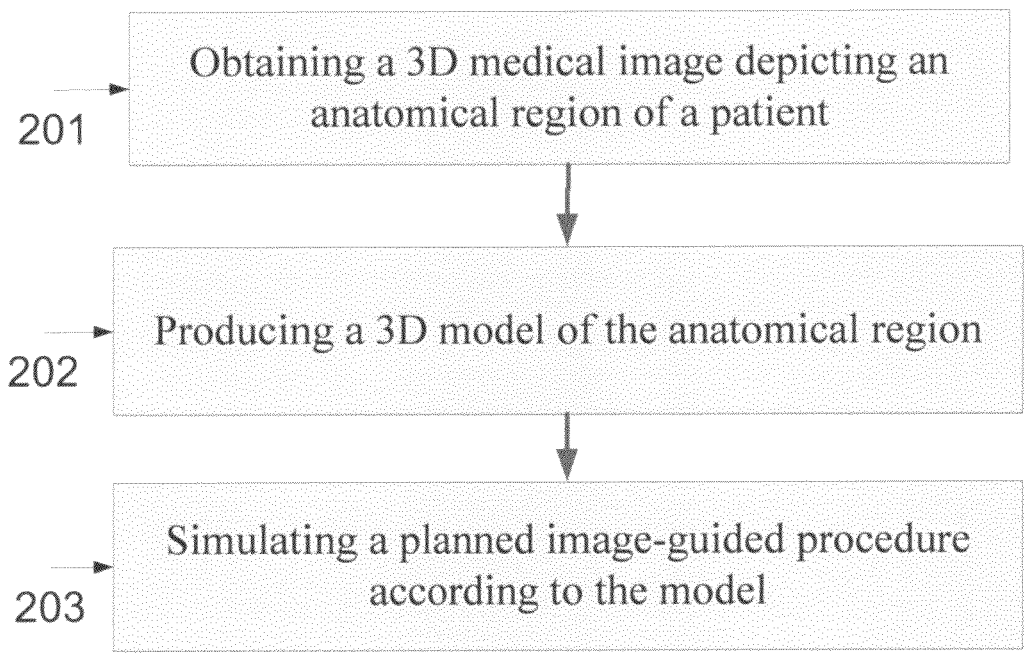
FIG. 6 is a flowchart of a method for performing a pre-operative simulation of an image-guided procedure, according to a preferred embodiment of present invention.

Reference is now made to FIG. 6, which is a flowchart of a method for performing a simulated image-guided procedure, according to one embodiment of present invention.

The method depicted in FIG. 6 allows a physician to conduct a clinical pre-operative simulation of the image guided procedure he or she is about to perform. Such a simulation allows the physician to take safe and unrushed clinical decisions based on a 3D medical image of the patient that is about to be operated on.

During the first step, as shown at 201, a 3D medical image depicting an organ of a patient is obtained. The 3D medical image has been taken using a medical imaging system and obtained, for example via a PACS server or a portable memory device, as described above. The 3D medical image depicts an organ of a patient that is about to be operated on. During the following step, as shown at 202, a 3D model of the anatomy is produced according to the received 3D medical image. The 3D model defines the boundaries of areas in the anatomy such as a certain tract. In the following step, as shown at 203, a simulation of an image-guided procedure on the patient is held according to the 3D model that has been constructed in the previous step. The simulation of the image-guided procedure allows a physician to prepare himself to the operative image-guided procedure. Based on the simulation, the physician can choose the fittest angles and the tools. Furthermore, the user can mark pitfalls, such as hard-to-navigate zones or misleading view angles in advance.

For example, if the simulated image-guided procedure is an angioplasty procedure, the physician can choose, in advance, the size and the type of the catheter, the balloon, and the stent he is going to use during the operation. Moreover, gaining acquaintance with the specific anatomy of the patient in advance may result in reducing contrast injection and X-ray exposure. In angioplasty procedure, for example, the duration of the X-ray exposure periods depends on the time it takes the physician to maneuver the catheter in the relevant anatomy region. If the physician already simulated the angioplasty procedure using the aforementioned system, he is already familiar with the specific region and therefore can easily maneuver the catheter during the actual angioplasty procedure.

It is expected that during the life of this patent many relevant devices and systems will be developed and the scope of the terms herein, particularly of the terms a 3D model, an imaging device, a simulating unit, motion detectors, a 3D medical image, and an image-guided procedure are intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An apparatus for simulating an image-guided procedure, comprising:

an input unit to receive a three-dimensional (3D) medical image specific to an actual patient undergoing a specific medical procedure obtained by a medical imaging system depicting an anatomical region of the patient undergoing the specific medical procedure, wherein said input unit is configured to receive a 3D data array composed as a pre-fetched and pre-parsed image, wherein the medical image is obtained after administering an intravenous contrast enhancement (ICE) component to the patient in order to improve precision of an automatic 3D segmentation process related to a soft tissue;

an anatomy-model generation unit for generating a 3D anatomical model of the anatomical region based on the received 3D medical image, wherein said anatomy-model generation unit comprises a 3D image segmentation unit, wherein said 3D image segmentation unit is configured to perform the automatic segmentation process on the 3D medical image specific to the patient for segmenting the received 3D images into anatomical structures, wherein the segmentation process is based on a segmentation procedure in which relevant voxels of the received 3D data array are isolated according to values of the voxels, wherein said segmentation procedure is adapted to segment a subset of scanned voxels from the 3D medical image wherein the values of the voxels in said subset is in a predefined range, wherein said automatic segmentation process comprises classification of data voxels according to respective anatomical parts of said anatomical region and registration of said anatomical region; and a simulating unit to simulate an image-guided procedure planned for said patient according to said 3D anatomical model, wherein said simulating unit comprises an intervention simulator device and a simulation module, wherein said intervention simulator device comprises a dummy interventional instrument, motion detectors, a movement calculation unit, an image displaying device and a force feedback mechanism, wherein said simulation module is configured to receive inputs from said motion detectors, analyze the inputs using said movement calculation unit to produce outcome, translate the outcome to visual and tactile outputs, and transfer the outputs to said image displaying device and said force feedback mechanism, and wherein said simulation module is further configured to receive the segmented 3D medical image from said anatomy-model generation unit, wherein the segmented 3D medical image is translated to a 3D model that simulates the anatomical region of the patient.

2. The apparatus of claim 1, where said 3D medical image is represented in digital imaging and communication in medicine (DICOM) format and said 3D anatomical model is presented by sets of data comprising a 3D spline description and polygonal meshes representation.

3. The apparatus of claim 1, wherein said 3D anatomical model is a model of a tract and said tract is a member of the following group: a vascular tract, a urinary tract, a gastrointestinal tract, and a fistula tract.

4. The apparatus of claim 1, wherein said 3D medical image is a member of the following group: computerized tomography (CT) scan images, magnetic resonance imager (MRI) scan images, ultrasound scan images, and positron emission tomography (PET)-CT scan images.

5. The apparatus of claim 1, wherein said planned image-guided procedure is an angioplasty procedure.

6. The apparatus of claim 1, further comprising a user interface operatively connected to said model generation unit, said user interface is to accept input data that identifies a location in the 3D medical image.

7. The apparatus of claim 1, wherein said simulated planned image-guided procedure is used as a study case during a learning process.

8. The apparatus of claim 1, wherein said simulated planned image-guided procedure is used to demonstrate a respective image-guided procedure to said patient.

9. The apparatus of claim 1, wherein said simulated planned image-guided procedure is used to document preparation to an operation.

10. The apparatus of claim 1, wherein said input unit is configured for receiving a four dimensional (4D) medical image, which is a set of consecutive 3D medical images that depicts said anatomical region during a time period, said model generation unit is configured for generating a 4D anatomical model according to said 4D medical image, said simulating unit is configured for simulating an image-guided procedure planned for said patient according to said 4D anatomical model.

11. The apparatus of claim 1, wherein said anatomical region is a member of a group comprising: an organ, a human body system, an area of an organ, a number of areas of an organ, a section of an organ, and a section of a human body system.

12. A method for performing a simulated image-guided procedure, said method comprising:

obtaining, by an input system, a three-dimensional (3D) medical image specific to an actual patient undergoing a specific medical procedure, depicting an anatomical region of the patient undergoing the specific medical procedure, wherein said input system is configured to receive a 3D data array composed as a pre-fetched and pre-parsed image, wherein the medical image is obtained after administering an intravenous contrast enhancement (ICE) component to the patient in order to improve precision of an automatic 3D segmentation process related to a soft tissue;

generating, via an anatomy-model generation unit, a 3D anatomical model of the anatomical region based on the received 3D medical image, wherein said anatomy-model generation unit comprises a 3D image segmentation unit;

performing, via said 3D image segmentation unit, the automatic 3D segmentation process on the 3D medical image specific to the patient for segmenting the received 3D images into anatomical structures, wherein the segmentation process is based on a segmentation procedure in which relevant voxels of the received 3D data array are isolated according to values of the voxels, wherein said segmentation procedure is adapted to segment a subset of scanned voxels from the 3D medical image wherein the values of the voxels in said subset is in a predefined range, wherein the automatic segmentation process comprises classifying data voxels according to respective anatomical parts of said anatomical region and registering said anatomical region; and simulating, via a simulating unit, an image-guided procedure planned for said patient according to said 3D anatomical model, wherein said simulating unit comprises an intervention simulator device and a simulation module, wherein said intervention simulator device comprises a dummy interventional instrument, motion detectors, movement calculation unit, an image displaying device and a force feedback mechanism, wherein said simulation module is configured to receive inputs from said motion detectors, analyze the inputs using said movement calculation unit to produce outcome, translate the outcome to visual and tactile outputs, and transfer the outputs to said image displaying device and said force feedback mechanism, and wherein said simulation module is further configured to receive the segmented 3D medical image from said anatomy-model generation unit, wherein the segmented 3D medical image is translated to a 3D model that simulates the anatomical region of the patient.

13. The method of claim 12, wherein said planned image-guided procedure is an angioplasty procedure.

14. The method of claim 12 comprising: receiving input data that identifies a location in the 3D medical image in relation to the automatic segmentation process.

15. The method of claim 12, further comprising a step of allowing a system user to mark labels for said planned image-guided procedure via a user interface.

16. The method of claim 12, wherein said planned image-guided procedure is an angioplasty procedure.

17. The method of claim 12, wherein said step of simulating is performed as a pre-operative surgical simulation.

18. The method of claim 12, wherein said 3D medical image includes blood vessels and said registering comprises registering centerlines, radii and inter-connectivity of said blood vessels.

19. The method of claim 12, wherein said 3D anatomical model is a tract model.

20. The method of claim 19, said tract model define a member of the following group:
 a vascular tract, a urinary tract, a gastrointestinal tract, and a fistula tract.

21. The method of claim 12, wherein said obtaining comprises obtaining a four dimensional (4D) medical image, which is a set of consecutive 3D medical images that depicts said anatomical region during a time period, said producing comprises producing a 4D model of said anatomical region according to said 4D medical image, said simulating is performed according to said 4D model.

22. The method of claim 12, wherein said anatomical region is a member of a group comprising: an organ, a human body system, an area of an organ, a number of areas of an organ, a section of an organ, and a section of a human body system.

\* \* \* \* \*